United States Patent
Camus et al.

(10) Patent No.: US 7,729,525 B2
(45) Date of Patent: Jun. 1, 2010

(54) IMAGE EVALUATION METHOD FOR TWO-DIMENSIONAL PROJECTION IMAGES AND ITEMS CORRESPONDING THERETO

(75) Inventors: Estelle Camus, Erlangen (DE); Thomas Redel, Poxdorf (DE)

(73) Assignee: Siemens Aktiengesellschat, Munich (DE)

( * ) Notice: Subject to any disclaimer, the term of this patent is extended or adjusted under 35 U.S.C. 154(b) by 958 days.

(21) Appl. No.: 11/505,552

(22) Filed: Aug. 17, 2006

(65) Prior Publication Data
US 2007/0041625 A1     Feb. 22, 2007

(30) Foreign Application Priority Data
Aug. 18, 2005   (DE) ................... 10 2005 039 189

(51) Int. Cl.
*G06K 9/00* (2006.01)
(52) U.S. Cl. .................... 382/130; 382/154
(58) Field of Classification Search ......... 382/128–132, 382/274; 600/425
See application file for complete search history.

(56) References Cited

U.S. PATENT DOCUMENTS

| | | | | |
|---|---|---|---|---|
| 5,636,636 A | * | 6/1997 | Kuhn et al. | 600/415 |
| 6,507,668 B1 | * | 1/2003 | Park | 382/169 |
| 6,978,112 B2 | * | 12/2005 | Kaburagi et al. | 399/366 |
| 2001/0012328 A1 | * | 8/2001 | Koppe et al. | 378/62 |
| 2002/0032583 A1 | * | 3/2002 | Joao | 705/2 |
| 2005/0111757 A1 | * | 5/2005 | Brackett et al. | 382/294 |
| 2005/0113680 A1 | * | 5/2005 | Ikeda et al. | 600/425 |

FOREIGN PATENT DOCUMENTS

| | | |
|---|---|---|
| EP | 1 345 154 A1 | 9/2003 |
| EP | 1 585 058 A2 | 10/2005 |
| WO | WO 97/17673 A1 | 5/1997 |
| WO | WO 99/47046 A1 | 9/1999 |
| WO | WO 03/046797 A2 | 6/2003 |
| WO | WO2005/048161 A1 | 5/2005 |

* cited by examiner

*Primary Examiner*—Samir A Ahmed
*Assistant Examiner*—Amara Abdi

(57) ABSTRACT

2-D projection images show the temporal course of the distribution of a contrast medium in an examination object containing a vascular system and the surroundings thereof. Each projection image has pixels with pixel values defined by the same areas of the examination object. A computer determines a 2-D evaluation image having pixels corresponding to those of the projection images and assigns each pixel in a sub-area to one of three types, vessel, perfused part of the surroundings or non-perfused part of the surroundings. The computer assigns an extent of a perfusion in the pixels of the evaluation image assigned the type of perfused part of the surroundings to the respective pixel. The type and extend are determined from the temporal course of the pixel values of the pixels of the projection image which is in a two-dimensional evaluation core defined by a respective pixel of the evaluation image.

19 Claims, 15 Drawing Sheets

| | Object vessel |
|---|---|
| | Object background |
| | Perfusion low |
| | Perfusion moderate |
| | Perfusion high |

SW1 =....
GZP =.....
F =........

| | Object vessel |
| | Object background |
| | Perfusion low |
| | Perfusion moderate |
| | Perfusion high |

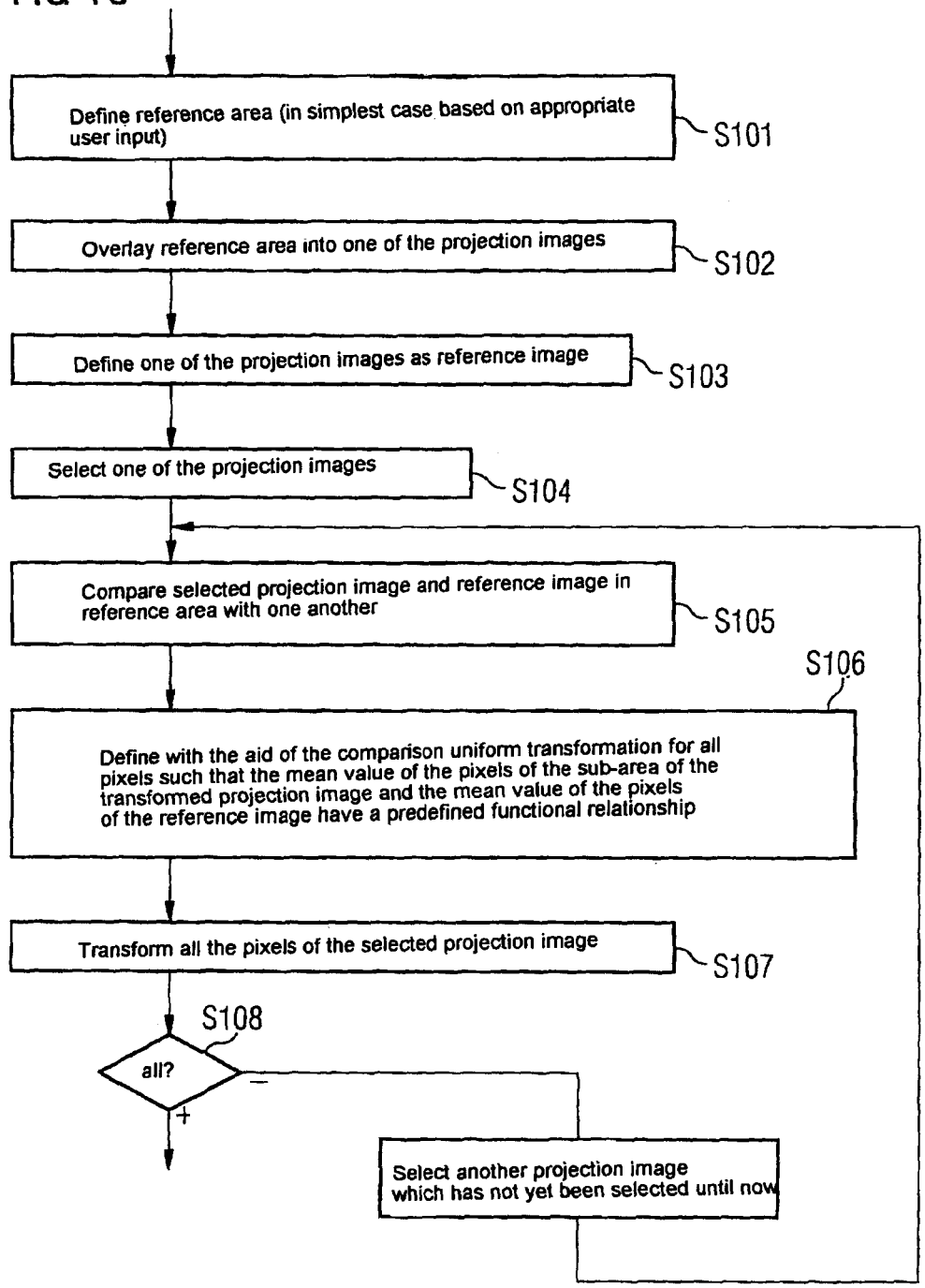

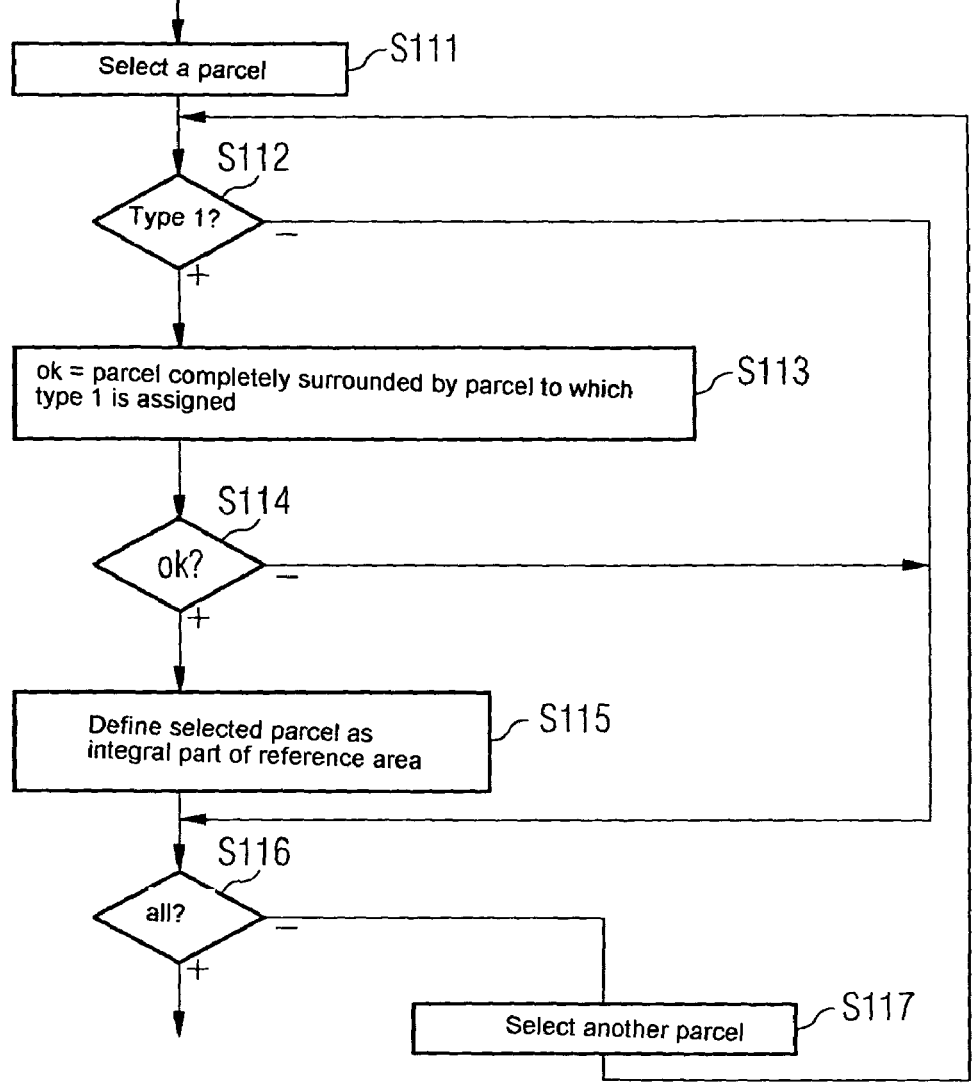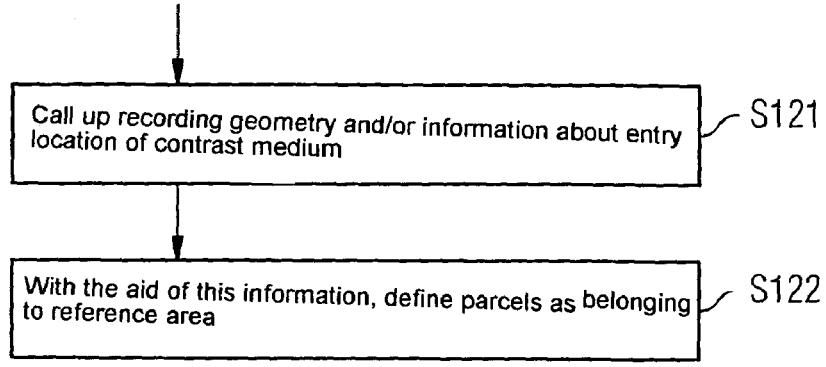

IMAGE EVALUATION METHOD FOR TWO-DIMENSIONAL PROJECTION IMAGES AND ITEMS CORRESPONDING THERETO

CROSS REFERENCE TO RELATED APPLICATIONS

This application claims priority of German application No. 10 2005 039 189.3 filed Aug. 18, 2005, which is incorporated by reference herein in its entirety.

FIELD OF THE INVENTION

The present invention relates to an image evaluation method for two-dimensional projection images which show the temporal course of the distribution of a contrast medium in an examination object, the examination object containing a vascular system and its surroundings, each projection image comprising a plurality of pixels having pixel values, the pixel values of pixels corresponding to one another in the projection images being defined by at least essentially locationally the same areas of the examination object.

The present invention relates furthermore to a data medium comprising a computer program stored on the data medium in machine-readable form for implementing an image evaluation method of this type and to a computer comprising a mass memory in which a computer program is filed, such that the computer executes an image evaluation method of this type when the computer program is called.

BACKGROUND OF THE INVENTION

Image evaluation methods of this type and the corresponding items are known.

Thus, for example, an image evaluation method of this type is known from the technical article "Quantitative Analyse von koronarangiographic Bildfolgen zur Bestimmung der Myokardperfusion" [Quantitative analysis of coronary angiographic image sequences for determining myocardial perfusion] by Urban Malsch et al., which appeared in "Bildverarbeitung für die Medizin 2003—Algorithmen—Systeme—Anwendungen" [Image processing for medicine 2003—algorithms—systems—applications], Springer Verlag, pages 81 to 85. In the case of this image evaluation method, a computer determines with the aid of the projection images a two-dimensional evaluation image which comprises a plurality of pixels, and outputs the evaluation image via a display device to a user. The pixels of the evaluation image correspond to those of the projection images. The computer undertakes, with the aid of the temporal course of the pixel values of the projection images, to assign a pixel value to the pixels of the evaluation image, the pixel value being characteristic of the time of maximum contrast change.

The doctrine of the above-mentioned technical article is described in the context of angiographic examinations of the coronary arteries of the human heart. This type of examination is one of the most important diagnostic tools in cardiology today. Additional information such as the determination of flow velocity or myocardial perfusion is further information which can in principle be obtained by means of angiography. The essential diagnostic evidence here is the perfusion of the myocardium.

Today, a number of other non-invasive methods of examination such as PET, SPECT, MR or contrast-medium-aided ultrasound have also become established. These methods of examination offer the facility for quantifying, in addition to other parameters, the perfusion status of the myocardium. These methods are generally applied in stable angina pectoris cases or in order to assess the risk after a myocardial infarction.

Arteriosclerosis, the trigger of myocardial infarctions, is not only a chronic disease which progresses slowly but also an extremely dynamic one. Here, the vascular wall not only becomes more rigid and thicker as a result of fat deposits, proliferations of smooth muscle cells and connective tissue-like rebuilding with calcification. Rather, active inflammatory processes with dissolving of tissue by matrix proteinases, apoptotic cell death and neovascularization determine the instability of the lining (plaque). A plaque rupture in a coronary artery, together with exposure of highly active arteriosclerotic material to flowing blood, triggers in extreme cases an acute coronary occlusion and, as a consequence, a myocardial infarction.

In the last few years, there have been increasing indications and evidence that a coronary plaque rupture does not always lead to a vascular occlusion and thus to a myocardial infarction, but may also lead to an embolization of arteriosclerotic material into the coronary microcirculation. Such a coronary microembolization can occur spontaneously as well as in the context of coronary interventions. In particular, a coronary intervention can also trigger a microembolization.

For an assessment of the therapeutic outcome of an intervention, it would therefore be advantageous to be able to monitor the improvement in perfusion and/or the occurrence of microembolization and microinfarctions during the actual intervention. It would consequently be advantageous if quantification of the perfusion were added to the other diagnostic parameters in the catheter laboratory, as this would make it possible to obtain all relevant information in one examination and thus to achieve an improvement in the monitoring of treatment.

Quantification of the perfusion of the myocardium by means of angiographic methods is, however, problematical, since the angiographically observable cardiac vessels have a diameter of almost a millimeter or more. These observable vessels terminate, however, in millions of tiny capillary vessels which have diameters of only a few micrometers. However, the flow dynamics and distribution in the capillary vessels are ultimately determined by the blood supply of the cardiac muscle. Drawing conclusions from macroscopic perfusion as to the dynamics of perfusion in the capillary vessels is therefore, strictly speaking, inadmissible, even though it is often done.

In order to record perfusion of the myocardium, various methods are known, in particular contrast echocardiography, magnetic resonance tomographic diagnostics and SPECT.

The echocardiographic determination of global and regional function is a firm component of non-invasive cardial functional diagnosis. Dynamic and pharmacological stress echo cardiography are used particularly in cases of ischemia and in vitality diagnostics and contribute to the indication of revascularizing measures in cases of chronic coronary heart diseases. Contrast-specific imaging methods have in this context recently enabled amplification of the signal from the intramyocardial blood pool, on the basis of which statements can be made with regard to myocardial perfusion. Current real-time methods even enable the simultaneous assessment of wall motion and myocardial perfusion with high spatial resolution.

Magnetic resonance tomographic diagnostic methods for coronary heart diseases are based on the evidence of pharmacologically induced perfusion or wall-motion disorders. Contrast-medium-aided first-pass perfusion measurement at rest and under pharmacological stress is the preferred procedure today for assessing myocardial perfusion. Here, drugs are used which lead to dilation of the unaffected coronary arteries and consequently, due to the raised blood flow in these dilated coronary arteries, result in an increase of the lower perfusion rate in the area supplied by a stenosis-affected coronary artery.

SPECT is a nuclear medical method. Tc-99m is nowadays used for this purpose as a contrast medium alongside thallium-201 chloride. Myocardial perfusion scintigraphy records the perfusion of the cardiac muscle under ergometric and pharmacological stress and at rest. In the process, reversible ischemias can be differentiated from permanent perfusion disorders or myocardial scars. A prerequisite for this method is an optimized tomographic examination technique.

Acute myocardial infarction represents a cardiological emergency situation in which a rapid diagnosis and treatment are required. In this emergency situation, an examination of the patient using magnetic resonance tomographic methods, SPECT methods or contrast echo cardiography is not as a general rule possible. Further problems emerge if for different reasons it has not been possible to carry out a perfusion measurement in advance. In all these cases angiographically based cardiac perfusion imaging would provide an important tool.

In angiographically based cardiac perfusion imaging, long recordings are made, the recordings lasting until such time as the contrast medium has flowed through the coronary arteries and is visible in the myocardium itself. This latter phase is referred to as the "myocardial blush". Assessment of the "myocardial blush" serves in providing evidence of the vascular supply to the heart and for example in rating the success of treatments and/or a risk profile for the patient.

In order to make the blood flow dynamics in large vessels and in the capillary vessels measurable and thereby comparable, various gradation systems are known which divide up the continuum of conditions into discrete classes. Some of these classifications describe the macroscopic circulation of blood, others the circulation of blood in the capillaries. The most-used classifications were drawn up by the scientific organization "Thrombolysis in Myocardial Infarction" (TIMI). These classifications are deemed to be the standard. In multi-center studies in which reproducible and comparable results are what particularly matters, the TIMI classifications are frequently used. The classifications are, however, complex and can be applied only in a time-consuming manner. They are therefore not generally used in routine clinical work.

By far the most frequently used method in the prior art is the visual assessment of "myocardial blush" on a screen. This procedure is often used for multi-center studies. A prerequisite for this procedure is that the angiographic recording is long enough in order to be able to see the entry and washout of the contrast medium. However, the visual assessment requires a lot of experience and is in practice carried out only by TIMI-blush experts, as they are known.

There are also various procedures known in which an attempt is made to carry out this subjective and personal visual assessment with the aid of computers. An example is to be found in the aforementioned technical article by Urban Malsch et al.

The procedure in the aforementioned technical article represents a good initial attempt but still displays shortcomings. For example, it is particularly necessary to identify the vessels of the vascular system in the projection images in order to mask out these vessels when analyzing the "myocardial blush". It is also necessary in the case of the procedure in the technical article to work with DSA images. This gives rise to a significant risk of artifacts, to avoid which compute-intensive methods are in turn required in order to compensate for motion.

SUMMARY OF THE INVENTION

The object of the present invention is to establish an image evaluation method and the items corresponding thereto, by means of which an identification of the vascular system is possible in a simple manner from the projection images themselves.

The object is achieved for an image evaluation method in that
 a computer determines with the aid of the projection images a two-dimensional evaluation image which has a plurality of pixels, and outputs said image to a user via a display device,
 the pixels of the evaluation image correspond to those of the projection images,
 the computer determines for each pixel in at least one sub-area of the evaluation image one of several mutually exclusive types and assigns it to the pixel,
 the computer determines the type from the temporal course of the pixel values of those pixels of the projection images which lie in a two-dimensional type evaluation core of the projection images determined by the respective pixel of the evaluation image,
 the type is characteristic of whether the respective pixel corresponds to a vessel in the vascular system, a perfused part of the surroundings of a vessel of the vascular system or a non-perfused part of the surroundings of a vessel of the vascular system,
 the computer also determines exclusively in the case of those of the pixels of the evaluation image to which it has assigned the type "perfused part of the surroundings" an extent of a perfusion of the corresponding area of the examination object and assigns it to the respective pixel and
 the computer determines the extent from the temporal course of the pixel values of those pixels of the projection images which lie in a two-dimensional basic extent-evaluation core of the projection images defined by the respective pixel of the evaluation image.

In contrast to the known prior art, it is consequently no longer necessary for the user to specify which area of the projection images corresponds to the myocardium. The assignment of types can instead be made from the projection images themselves.

Corresponding hereto, the object in respect of the data medium or the computer is achieved in that a computer program for implementing such an image evaluation method is stored on the data medium or in that such a computer program is filed in the mass memory of the computer so that the computer executes this image evaluation method when the computer program is called. The image evaluation method according to the invention is universally applicable. It is therefore applicable in particular also where the examination object does not move. An example of such an examination object is the human brain, in which the same perfusion problems can occur as in the human heart. These perfusion problems are known, where they occur acutely, under the heading 'stroke'. As a general rule, however, the examination object is an iteratively moving examination object. In this case, firstly a series of images is recorded and fed to the computer. Phase information about the examination object is assigned to each image of the series. The projection images are then selected from this series, care being taken to ensure that the phase information assigned to the projection images deviates by no more than one phase boundary from a reference phase. The computer can receive both the reference phase and the phase boundary from a user.

The computer preferably determines the number of projection images and outputs it to the user via the display device. For the user, a visual check is thus possible as to whether the reference phase and/or the phase boundary are defined well. Optionally, the total number of recorded iterations of the examination object can additionally be output.

After the projection images have been selected, it is possible for the computer to receive from the user a selection of one of the projection images and for the computer to output to the user via the display device the selected projection image together with the phase information assigned to this projection image and/or together with the deviation of the phase information assigned to this projection image from the reference phase. In this way, the user can see how large the deviation of the phase information of this projection image from the reference phase is.

The sub-area is preferably marked as such in one of the projection images or in the evaluation image, for example by means of a black outline. It can then easily be recognized by the user which area is specified as the sub-area.

The sub-area can be predetermined. Preferably, however, the computer receives it from the user, as the image evaluation method according to the invention then works particularly flexibly.

The assignment of types is particularly simple if the computer subdivides at least the sub-area of the evaluation image into type parcels of several pixels each and performs the assignment of types parcel by parcel. The computation effort for the assignment of types is then reduced by the factor N, where N is the number of pixels per type parcel. Usually, small rectangles (particularly squares), small regular triangles or small regular hexagons are used as type parcels.

The computer preferably determines for each projection image the weighted or unweighted mean value of the type evaluation core and performs the assignment of types with the aid of the temporal course of the mean value. The image evaluation method is then on the one hand relatively simple, and on the other very reliable and robust. The type evaluation core may correspond here in particular to the respective type parcel.

The image evaluation method according to the invention produces particularly optimum results where the computer determines a maximum change in the mean value of the type evaluation core relative to the mean value of the temporally first type evaluation core and assigns the type "non-perfused part of the surroundings" to the respective pixel of the evaluation image if the maximum change is less than a first threshold value. Otherwise, either the type "perfused part of the surroundings" or the type "vessel" is assigned to the respective pixel of the evaluation image.

The first threshold value can be fixed and be the same for all the pixels. Preferably, however, the first threshold value depends on a user input and/or on the mean value of the temporally first type evaluation core. For example, a percentage of the mean value of the temporally first type evaluation core can be used as a first threshold value (Dependency on the mean value of the temporally first type evaluation core), the percentage depending on the user input.

The computer preferably determines, if the maximum change of the mean value exceeds the first threshold value, the temporally earliest projection image in which the difference of the mean value of the type evaluation core of this projection image and of the mean value of the type evaluation core of the temporally first projection image exceeds the first threshold value. Depending on whether the time of the temporally earliest projection image lies before or after a limit time, the computer then immediately assigns the type "vessel" or "perfused part of the surroundings" to the respective pixel of the evaluation image.

It is possible for a fixed limit time to be specified. Preferably, however, the limit time will depend on a user input.

The computer preferably determines the projection image lying closest in time to the limit time and outputs it via the display device to the user, as in this way the user has the opportunity to check visually the limit time.

If the computer subdivides at least the sub-area of the evaluation image into extent parcels, each of several pixels, and performs the extent assignment on a parcel-by-parcel basis, the computation effort can be reduced.

The image evaluation method according to the invention can be implemented particularly simply if the computer determines for each projection image the weighted or unweighted mean value of the basic extent-evaluation core and performs the extent assignment with the aid of the temporal course of the mean value.

The basic extent-evaluation core preferably corresponds to the respective extent parcel.

The computer preferably determines the extent of the perfusion with the aid of at least one of the following variables:
  time period during which a change in the mean value exceeds the first threshold value;
  time period of the increase in the change in the mean value;
  time period of the reduction in the change in the mean value;
  maximum change in the mean value;
  time of maximum change in the mean value;
  time period until commencement of the change in the mean value.

The computer preferably also determines a value which is characteristic of a period during which the change in the mean value exceeds a second threshold value, and compares this value with a minimum time, as it is then possible for the computer to ignore the basic extent-evaluation core for the corresponding projection images if the period lies below a minimum duration. In particular, it is in this way possible to make corrections if the change in the mean value exceeds the second threshold value only for one or two of the projection images. These are then with a high degree of probability "outliers".

If the computer ignores basic extent-evaluation cores of projection images, the computer will preferably determine with the aid of those basic extent-evaluation cores which lie immediately before and/or after the ignored basic extent-evaluation cores replacement extent-evaluation cores, replace the ignored basic extent-evaluation cores with the replacement extent-evaluation cores and then perform the extent assignment again.

If the basic extent-evaluation core is identical with the type evaluation core, the image evaluation method according to the invention is made easier.

A very precise evaluation of the projection images, and yet one that is optimized in terms of computing time, emerges if the computer
  determines those pixels of the evaluation image to which it has assigned the type "perfused part of the surroundings", and which are, within a predefined minimum distance, surrounded exclusively by pixels to which it has also assigned the type "perfused part of the surroundings", and performs a repeat extent assignment with the aid of the temporal course of the pixel values of those pixels of the projection images which lie in a two-dimensional additional extent evaluation core of the projection images, determined by the respective pixel of the evaluation image, the respective additional extent evaluation core being contained in the corresponding basic extent-evaluation core.

The computer preferably converts with the aid of an assignment rule at least the extent of the perfusion into color values and outputs the evaluation image in the form of an appropriately color-coded representation to the user via the display device. The extent of the perfusion is then particularly easy for the user to grasp intuitively. Optionally, the two other types "non-perfused part of the surroundings" and "vessel" can also be appropriately color-coded.

If the computer outputs the assignment rule together with the color-coded representation via the display device to the user, the extent of the perfusion is easier for the user to assign. For example, the assignment rule can be overlaid in the evaluation image or shown alongside the evaluation image—for example in its own separate window.

The image evaluation method according to the invention can be optimized still further if one of the projection images is defined as a reference image, the computer compares a reference area of the projection images with a corresponding reference area of the reference image, the computer determines from the comparison a transformation of pixel values valid for all the pixels of the respective projection image such that the mean value of the pixel values of the reference area of the transformed projection image and the mean value of the pixel values of the reference area of the reference image have a predefined functional relationship, and the computer transforms the pixel values of the respective projection image in accordance with this transformation. Differences of intensity in the projection images which emerge due to operating parameters not being held constant in the recording of the projection images can then also be at least partially compensated for.

The computer preferably overlays the reference area in one of the projection images or in the evaluation image. The user can then immediately grasp intuitively which image area is being used to define the transformation. Based upon his intellectual understanding of the displayed image, the user can therefore assess whether the reference area is properly defined.

It is possible for the computer to determine the reference area automatically. For example, it is possible for the computer to determine the reference area from the pixels of the evaluation image to which it has assigned the type "non-perfused part of the surroundings". Alternatively or additionally, the computer can take into account when determining the reference area information about the recording geometry underlying the projection images and the location of entry of the contrast medium into the examination object.

As an alternative to determination of the reference area by the computer, it is of course also possible for the computer to receive the reference area from the user.

If the computer receives an instruction from the user to select a pixel or a group of pixels in the evaluation image and the computer then determines the temporal course of the mean value of the pixel values of those areas of the projection images with the aid of which the computer has determined the extent of perfusion of the selected pixel or of the selected group of pixels and outputs this via the display device to the user, it is possible for the user to carry out in a simple manner an even more in-depth and detailed evaluation of the projection images.

The computer preferably outputs to the user via the display device at least the defining criteria with the aid of which it has defined the type assignment of at least the sub-area of the evaluation image, together with the evaluation image. In this way, simple control by the user is possible. The defining criteria are preferably modifiable by the user interactively, and the computer determines the evaluation image afresh in the event of a change in the defining criteria. Simple optimization of the defining criteria by the user is then possible.

If the computer overlays one of the projection images into the evaluation image, the position of the vessels can be detected in a simple manner. This makes it easy for the user to check whether the computer has performed the type assignment correctly.

If, on the basis of a request to that effect by the user, the computer automatically generates a report from the evaluation image, assigns the evaluation image and the report to the projection images and archives the projection images, the evaluation image and the report as a unit, the user is relieved of this work.

BRIEF DESCRIPTION OF THE DRAWINGS

Further advantages and details will emerge from the description below of an exemplary embodiment in conjunction with the drawings, in which in schematic representation:

FIG. 16 shows a further temporal course of a mean value and FIGS. 17 to 20 show flow diagrams.

DETAILED DESCRIPTION OF THE INVENTION

Figure 1:
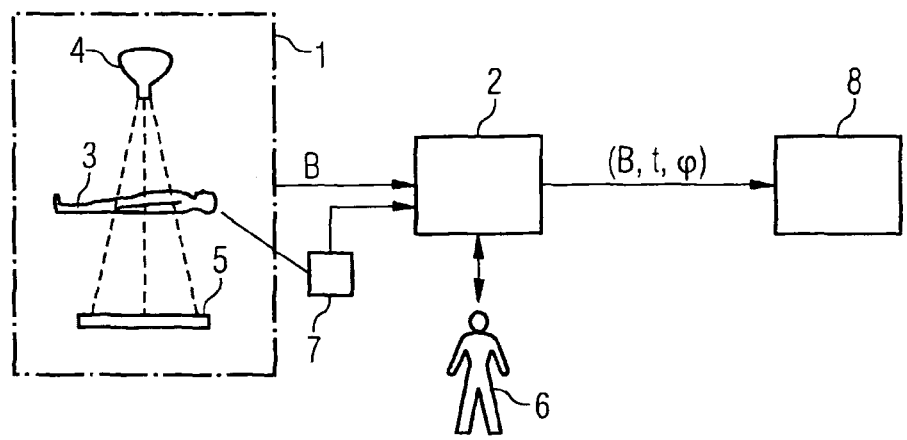
FIG. 1 shows a block diagram of a recording arrangement, a control computer and an evaluation device.

In accordance with FIG. 1, a recording arrangement 1 is controlled by a control device 2. By means of the recording arrangement 1, images B of an examination object 3 are recorded. In the present case, in which the examination object 3 is a person, images B of the heart or of the brain of the person 3 are recorded, for example.

In order to record the images B, the recording arrangement 1 comprises a radiation source 4, here e.g. an X-ray source 4, and a corresponding detector 5.

Figure 2:
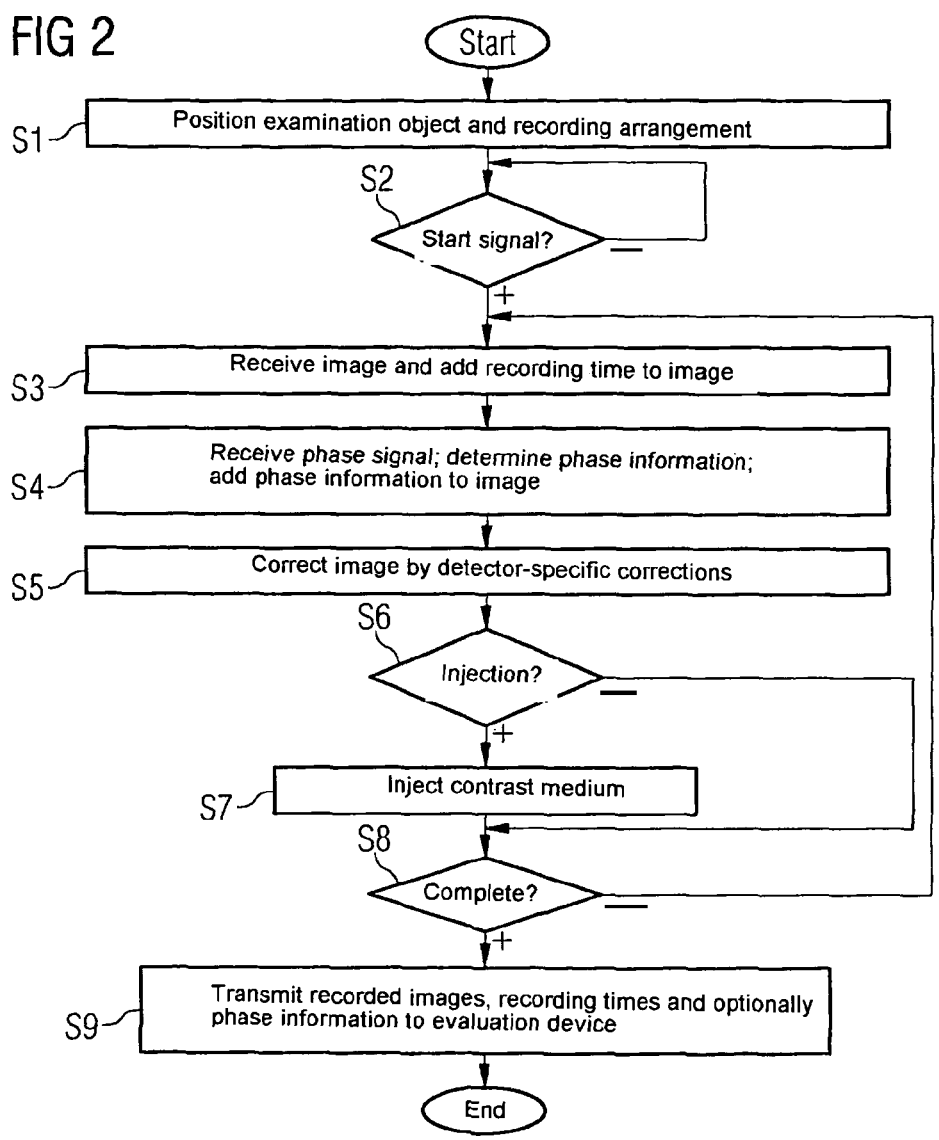
FIG. 2 shows a flow diagram.

In order to record the images B, the examination object 3 and the recording arrangement 1 are firstly positioned in a step S1, as shown in FIG. 2. The positioning can depend in particular on which region (heart, brain, etc.) of the examination object 3 is to be recorded and which part of the region is specifically relevant, for example which coronary artery (RCA, LAD, LCX) is to be observed. Step S1 can alternatively be carried out purely manually by a user 6, fully automatically by the control device 2 or else by the user 6 assisted by the control device 2.

The performance of step S1 may be connected with a recording of control images. However, this not relevant in the scope of the present invention and is therefore not explained in detail.

The control device 2 then waits in a step S2 for a start signal from the user 6. After the start signal has been received, the detector 5 records an image B of the examination object 3 and feeds it to the control device 2. The control device 2 receives the image B in a step S3 and adds to the image B a corresponding recording time t. If the examination object 3 or the relevant part of the examination object 3 should move iteratively, the control device 2 receives furthermore in a step S4 from a corresponding recording device 7 a phase signal of the examination object 3. Also as part of step S4, the control device 2 then determines a corresponding phase information $\phi$ and likewise adds the phase information $\phi$ to the recorded image B. For example, the control device 2 can, as part of step S4, receive an EKG signal and from it derive the phase information $\phi$. Also, the control device 2 can optionally control the recording arrangement 1 with the aid of the phase signal supplied such that the recording of the images B takes place only at one or more predefined phase positions of the examination object 3, for example only 0.3 and 0.6 seconds after the R-wave of the EKG signal.

As a rule, the examination object 3 is not influenced externally in its iterative motion. If, for example, the heart of the person 3 is beating very irregularly, however, an external stimulation of the heart by means of a cardiac pacemaker can deliberately be carried out in order to forcibly bring about a regular heartbeat.

In a step S5, the control device 2 corrects the recorded image B. In doing so, the control device 2 preferably corrects the recorded image B exclusively through detector-specific corrections but does not carry out any more far-reaching image processing. For example, it does not apply any noise-reduction methods.

In a step S6, a check is carried out to establish whether an injection of a contrast medium is to be made. If this check is answered in the affirmative, the contrast medium is injected into the examination object 3 in a step S7. Steps S6 and S7 can—like step S1—be performed by the user 6 himself/herself, performed fully automatically by the control device 2 or else performed by the user 6 but aided by the control device 2.

In a step S8, the control device 2 checks whether the recording of the images B is to be terminated. If this is not the case, the control device 2 goes back to step S3. Otherwise, it transmits in a step S9 the recorded images B, preferably corrected by means of detector-specific corrections, their recording times t and optionally also their phase information $\phi$ to an evaluation device 8. As an alternative to transmission of the images B, the recording times t and the phase information $\phi$ as part of the subordinate step S9, the transmission could of course also be carried out image by image, i.e. between steps S5 and S6.

The method outlined above was sketched out only roughly, as, within the scope of the present invention, it is of only secondary importance. Thus, for example, the—manual, fully automatic or computer-aided—adjustment of the recording parameters of the recording arrangement 1 (operating voltage of the radiation source 4, image rate, image pre-processing, positioning, etc.) was taken as self-evident. Any calibration of the recording arrangement 1 which may optionally be necessary can also be carried out. It also goes without saying that the recording of the images B has to be carried out over a sufficiently long period, namely starting before the injection of the contrast medium and ending after the washout of the contrast medium.

Figure 3:
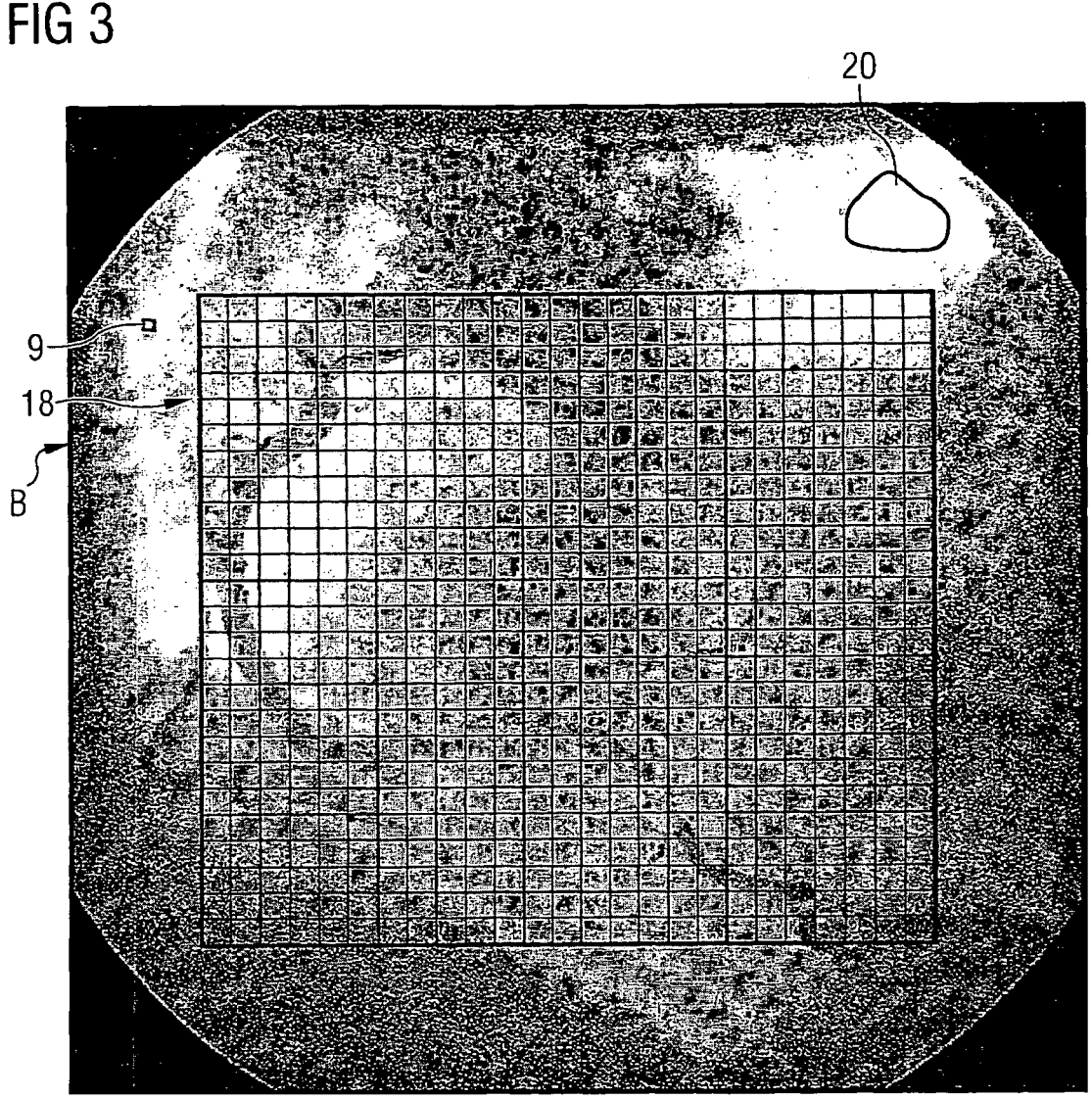
FIG. 3 shows an example of a projection image.

FIG. 3 shows by way of example one of the recorded images B. It can immediately be seen from FIG. 3 that the image B is two-dimensional and consequently contains a plurality of pixels 9. The resolution of the image B is even so high that the individual pixels 9 are no longer recognizable in the image B shown. Purely by way of example, one of the pixels 9 is marked with the reference symbol 9. Each pixel 9 has a pixel value which lies e.g. between 0 and 255 ($=2^8-1$). It can also be seen from FIG. 3 that the examination object 3 contains a vascular system and its surroundings. Due to the fact that in their entirety the images B form a time sequence, the images B consequently also show simultaneously the temporal course of the distribution of the contrast medium in the examination object 3.

If the examination object 3 was motionless during the recording of the images B (for example because images B of the brain of the person 3 were recorded) or if, due to appropriate triggering of the recording (for example, always 0.6 seconds after the R-wave of the EKG), the images B constantly show the examination object 3 in the same phase position, the image recording as such already guarantees that the pixel values of pixels 9 corresponding to one another in the images B are defined by at least essentially locationally the same areas of the examination object 3. In this case, all the recorded images B can be defined as projection images B within the meaning of the comments that follow. Otherwise, an appropriate selection must be made. This is explained in detail below in conjunction with FIGS. 4 and 5.

Figure 4:
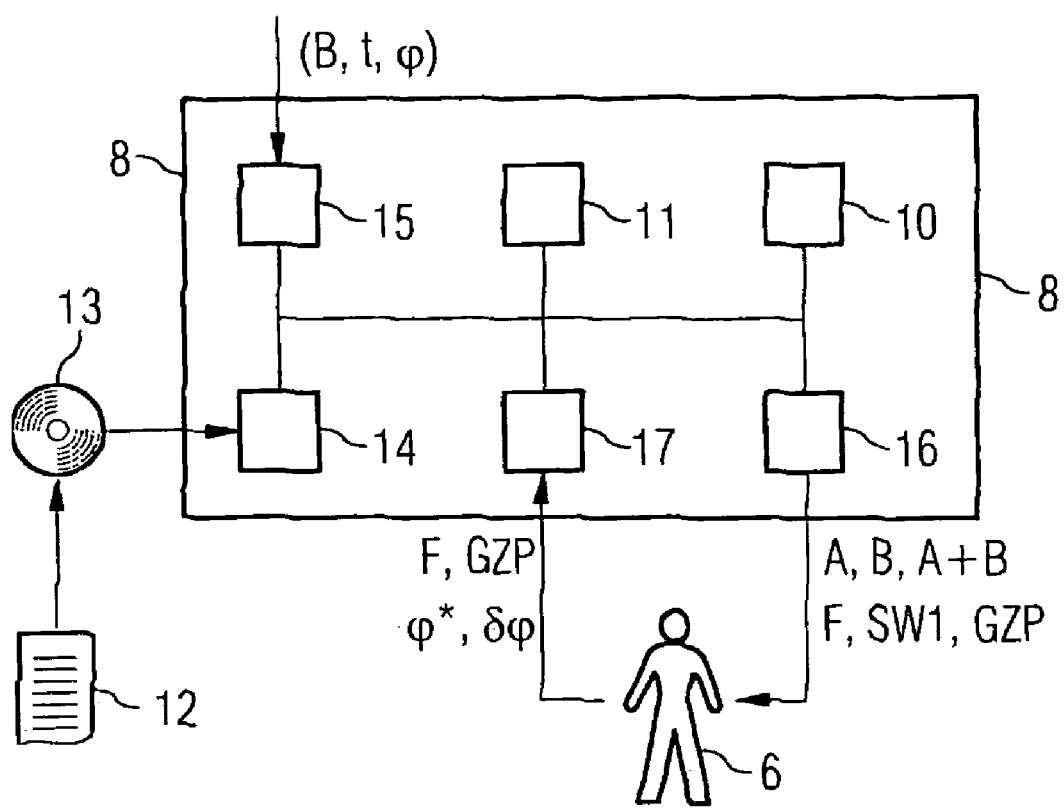
FIG. 4 shows a block diagram of an evaluation device.

In accordance with FIG. 4, the evaluation device 8—which can in principle be identical with the control device 2—comprises inter alia an arithmetic-logic unit 10 and a mass memory 11. A computer program 12 is filed in the mass memory 11. When the computer program 12 is called, the evaluation device 8 executes an image evaluation method which is described in detail below. Consequently, the evaluation device 8 constitutes a computer within the meaning of the present invention. It should, however, also be mentioned in advance that the computer program 12 must of course previously have been routed to the evaluation device 8. This routing can, for example, be carried out by means of a suitable data medium 13 on which the computer program 12 is likewise stored. This data medium 13 is introduced to a suitable interface 14 of the evaluation device 8 so that the computer program 12 stored on the data medium 13 can be read out and filed in the mass memory 11 of the evaluation device 8.

Figure 5:
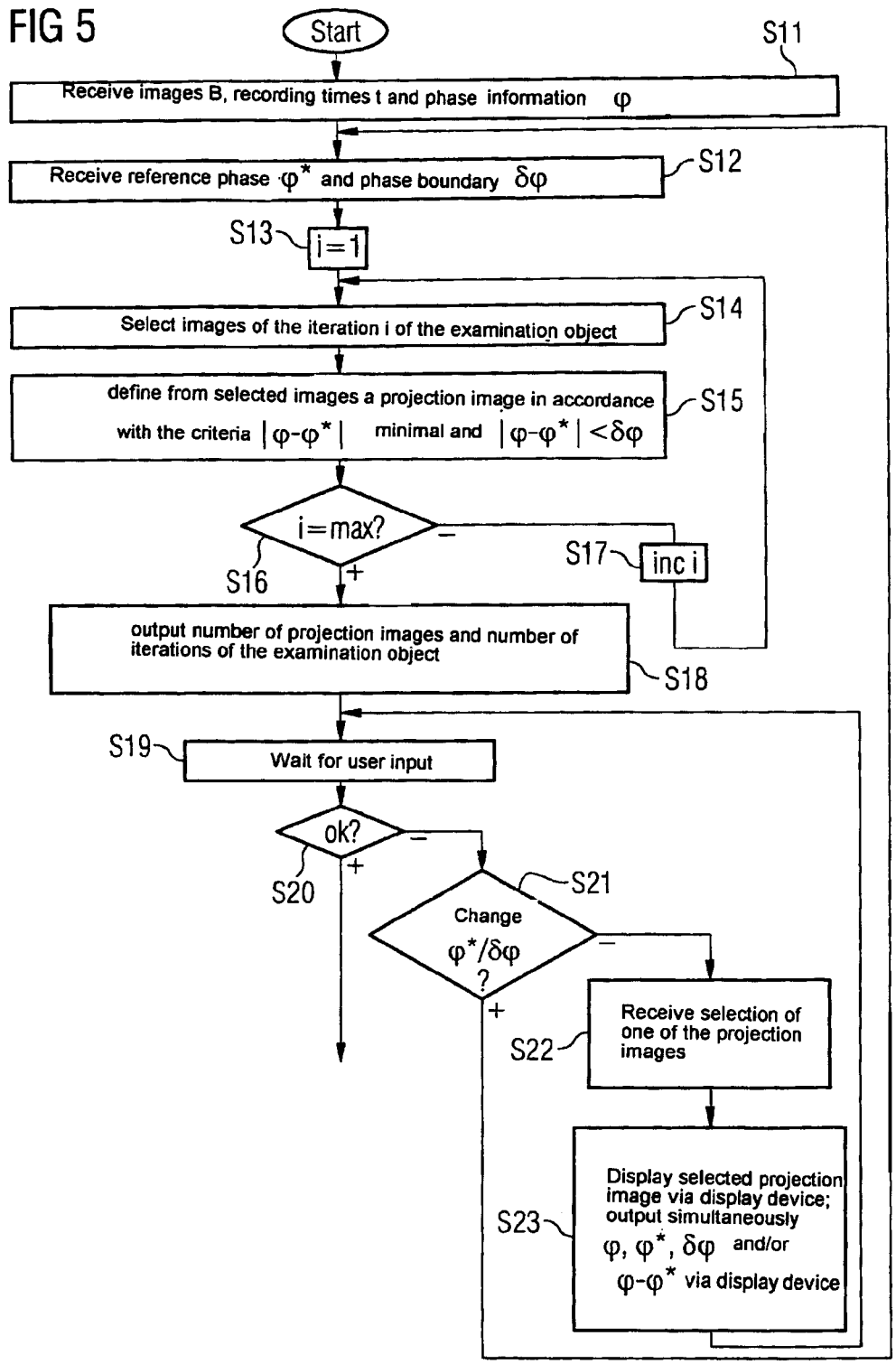
FIGS. 5 and 6 show flow diagrams.

In accordance with FIG. 5, the images B themselves are fed to the evaluation device 8 in a step S11 via an appropriate interface 15. The same applies to the corresponding recording times t and the assigned phase information $\phi$. In order to select the projection images B from the recorded series of images B, however, the appropriate selection criteria $\phi^*$, $\delta\phi$ must also be known to the evaluation device 8, namely a reference phase position $\phi^*$ and a phase boundary $\delta\phi$. It is possible here for the reference phase $\phi^*$ and the phase boundary $\delta\phi$ to be stored within the evaluation device 8. Preferably, however, the reference phase $\phi^*$ and the phase boundary $\delta\phi$ are specified for the evaluation device 8 in a step S12 by the user 6 via an appropriate input device 17. For example, it is possible for the user 6, by means of appropriate inputs, to scroll through the recorded sequence of images B and to select one of the images B. The phase information $\phi$ of the image B selected in this way then defines the reference phase $\phi^*$, and the distance to the immediately succeeding and immediately preceding image B the phase boundary $\delta\phi$. However, it is of course also possible for the user 6 to specify the appropriate values φ*, δφ explicitly by means of numerical values. Finally, it is also possible for the EKG signal to be output via a display device 16 to the user 6 and for the user 6 to place appropriate markers in the EKG signal. In all cases, the user 6 can specify the values φ* and δφ alternatively as absolute time values or as relative phase values.

In steps S13 to S17, the actual selection of the projection images B from the entire series of images B is made. To this end, firstly in a step S13 an index i is set to the value one. The evaluation device 8 then selects in step S14 the images B of the iteration i of the examination object 3. Within the images B now selected, the evaluation device 8 now generally defines one (exceptionally also none) of the images B as a projection image B. It looks in step S15 firstly for the particular image among the selected images B in which the size of the difference of the phase information φ relative to the reference phase φ* is minimal. It then checks whether this difference is less than the phase boundary δφ. If the evaluation device 8 can determine such an image B, it defines this image B in step S15 as the projection image B for the respective iteration i. If it cannot determine any such image B, it notes this appropriately.

In step S16, the evaluation device 8 checks whether the index i has already reached its maximum value. If this is not the case, the evaluation device 8 increments the index in step S17 and goes back to step S14. Otherwise, the definition of the projection images B is complete.

This procedure, which is an integral part of the present invention ensures that the pixel values of pixels corresponding to one another 9 in the projection images B are also defined, where the examination object 3 has moved iteratively during the recording of the entire series of images B, by at least essentially locationally the same areas of the examination object 3.

In a step S18, the evaluation device 8 outputs the number of projection images B determined and the number of iterations of the examination object 3 to the user 6 via the display device 16. Said user can thus recognize whether he/she has made a good selection in respect of the reference phase φ* and/or the phase boundary δφ.

In a step S19, the evaluation device 8 next waits for a user input. If such an input has been made, the evaluation device 8 checks in a step S20 whether this input was a confirmation by the user 6. If this is the case, the selection of projection images B is complete and the process can continue with the actual image evaluation method.

Otherwise, the evaluation device 8 checks in a step S21 whether the user 6 has input a request for the reference phase φ* and/or the phase boundary δφ to be changed. If this is the case, the evaluation device 8 goes back to step S12.

Otherwise, the user 6 has input a request for one of the projection images B to be displayed. In this case, the evaluation device 8 receives from the user 6 in a step S22 a corresponding selection. In a step S23, it then displays the selected projection image B on the display device 16. It also outputs together with the selected projection image B the corresponding phase information φ of the selected projection image B, the reference phase φ*, their difference and the phase boundary δφ to the user 6 via the display device 16. It then goes back to step S19. It would optionally be possible to display an overall representation of the phase course and to display the phase information φ of all the projection images B simultaneously.

For the sake of completeness, it should be mentioned that steps S12 to S23 are appropriate and/or necessary only where a selection of projection images B has to be made from the entire series of images B. If, on the other hand, the recorded images B are all suitable a priori, steps S12 to S23 can be omitted.

It should furthermore be mentioned that as an alternative to the procedure described above in conjunction with FIG. 5, it is also possible to stipulate in advance suitable intervals for the phase information φ and to determine for each interval the number of possible projection images B. The evaluation device 8 can in this case output a list or table with the aid of which the user can recognize how many projection images B are available to him/her and for which phase interval respectively. In this case, the user 6 has only to select the phase interval desired by him/her.

Figure 6:
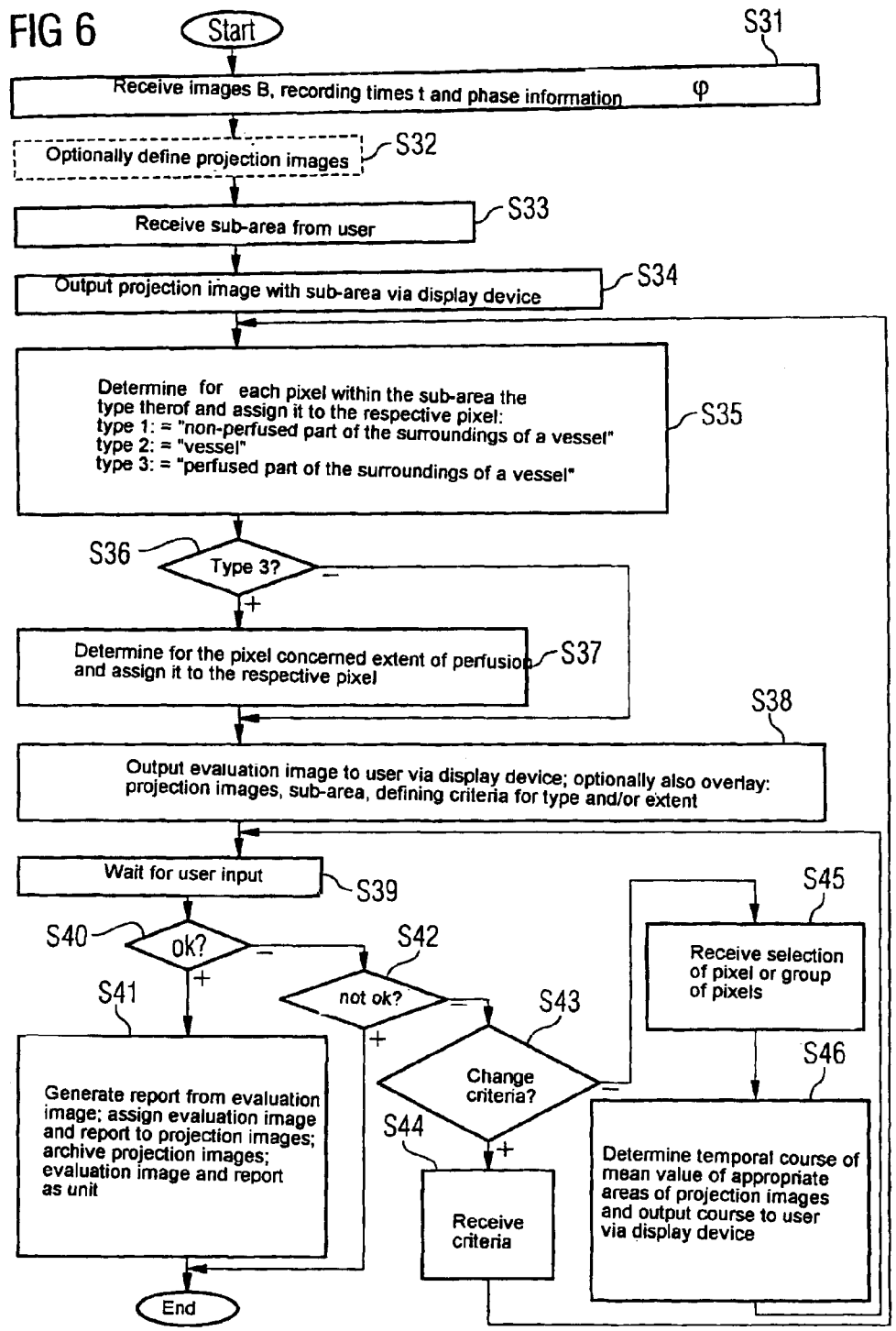

When the selection of projection images B from the entire series of images B is complete, the process continues with FIG. 6. Steps S31 and S32 in FIG. 6 correspond on the one hand to step S11 and on the other to steps S12 to S23 in FIG. 5. Since step S32 is, as previously mentioned, only optional, it is represented in FIG. 6 by dashed lines only.

In a step S33, the evaluation device 8 receives from the user 6 a sub-area 18. The evaluation device 8 overlays this sub-area 18 in a step S34 into one of the projection images B and outputs this projection image B together with the marking of the sub-area 18 to the user 6 via the display device 16. This can also be seen from FIG. 3. The sub-area 18 corresponds to the black frame in FIG. 3.

In a step S35 the computer 8 then determines for each pixel 9 which lies within the specified sub-area 18 the type thereof. Type 1 corresponds to the non-perfused part of the surroundings of a vessel. Type 2 corresponds to a vessel and type 3 to the perfused part of the surroundings of a vessel.

In a step S36, the evaluation device 8 checks for each pixel 9 within the sub-areas 18 whether this pixel 9 was assigned to type 3. If this is the case, the evaluation device 8 determines for the respective pixel 9 in a step S37 an extent of the perfusion and assigns the extent determined to the pixel 9 concerned.

The assignment of the respective type and optionally also of the extent of the perfusion to the individual pixels 9 defines an evaluation image A. Due to the way in which the evaluation image A is generated, each pixel 9 of the evaluation image A matches the corresponding pixels 9 of the projection images B. In particular, the evaluation image A is thus also two-dimensional and comprises a plurality of pixels 9. The evaluation device 8 outputs this evaluation image A as part of a step S38 to the user 6 via the display device 16.

Steps S35 to S37, which relate to the actual core of the present invention, will be discussed in detail again later.

Figure 7:
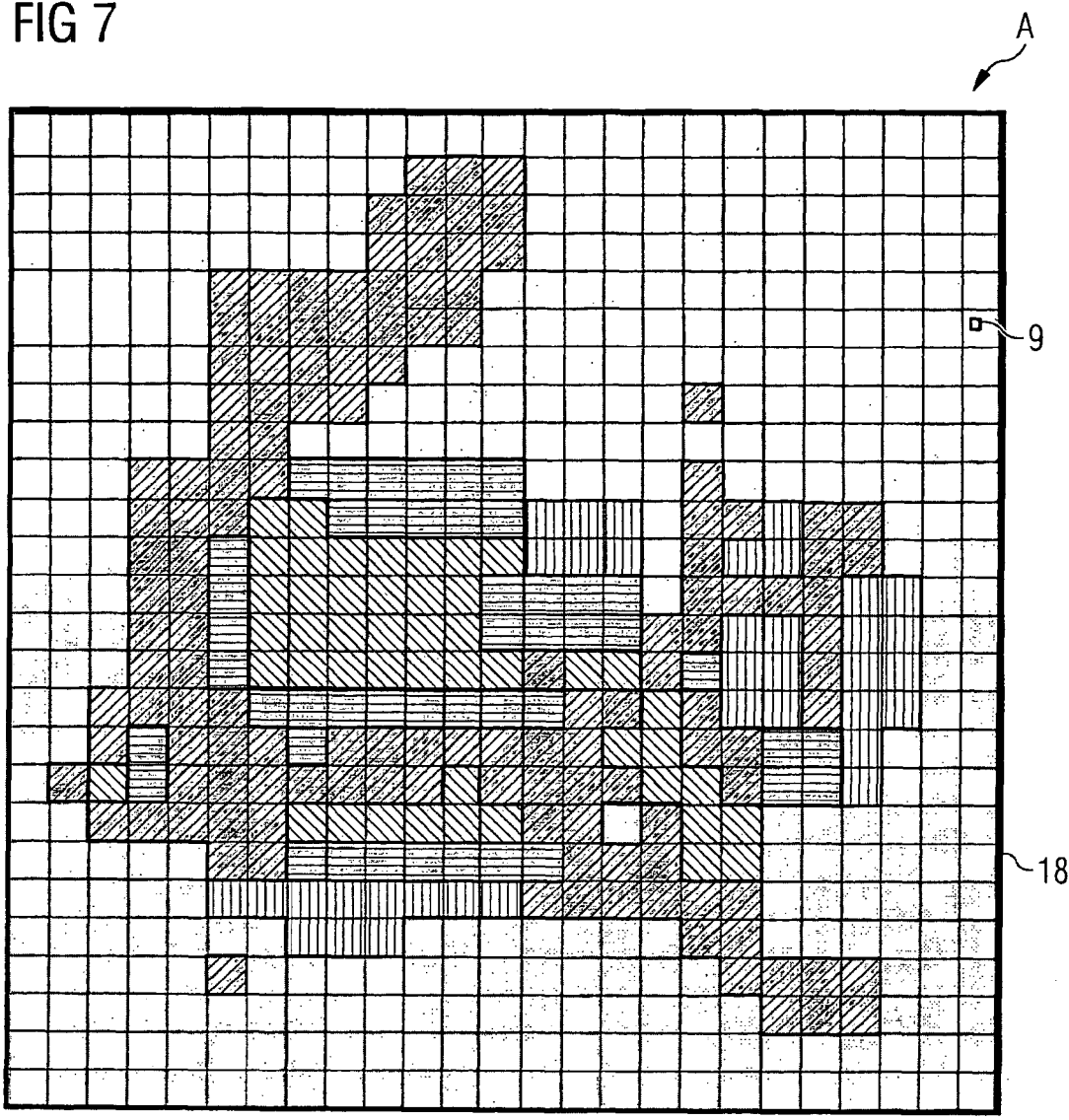
FIG. 7 shows an evaluation image.

FIG. 7 shows such an evaluation image A. In accordance with FIG. 7, the evaluation device 8 has converted the extent of the perfusion and also the type into color values with the aid of an assignment rule. The evaluation device 8 consequently outputs the evaluation image A in the form of a color-coded representation to the user 6 via the display device 16. At the same time, the evaluation device 8 can also optionally output the assignment rule together with the color-coded representation to the user 6 via the display device 16.

Figure 8:
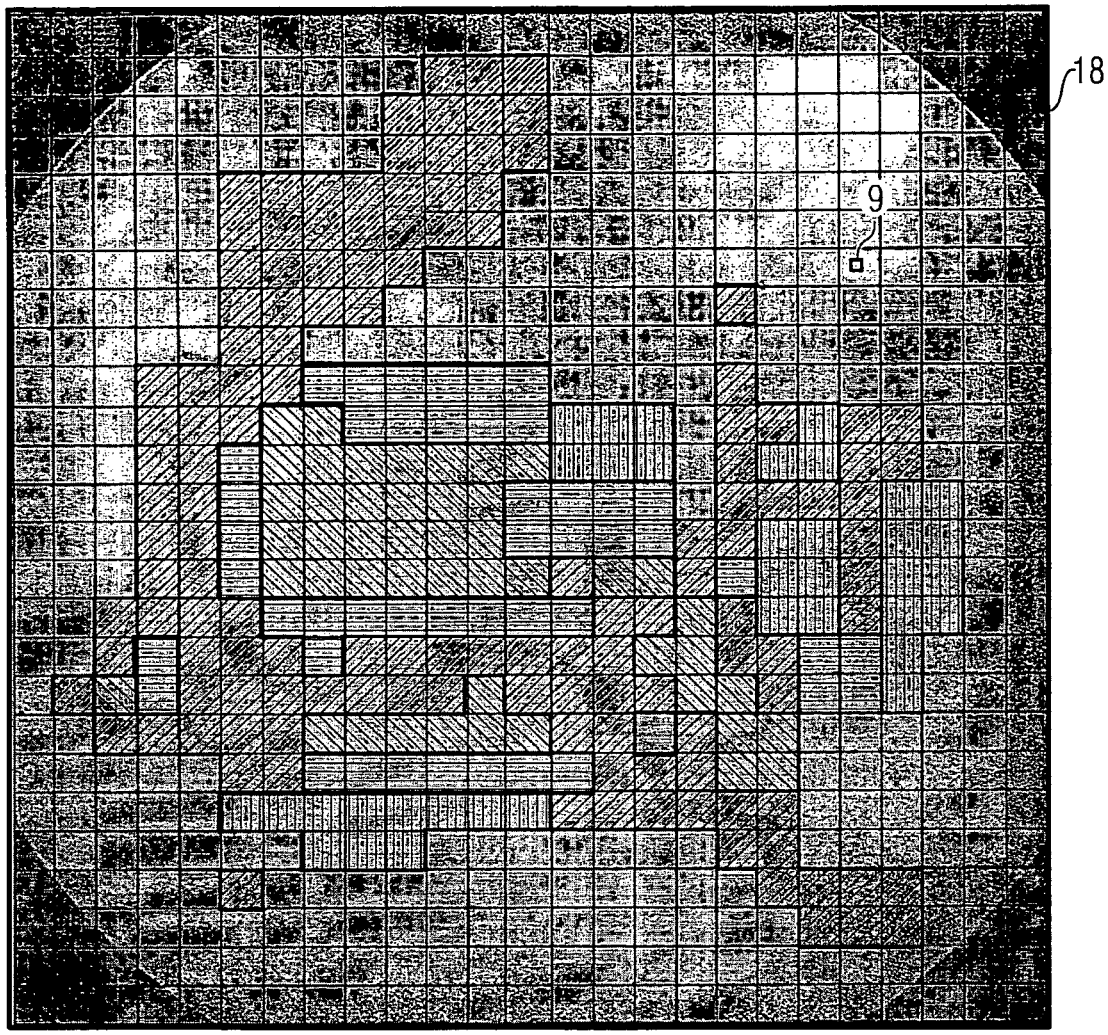
FIG. 8 shows the evaluation image from FIG. 7 with an overlaid projection image.

As an alternative to the representation as shown in FIG. 7, it is also possible, as shown in FIG. 8, to overlay one of the projection images B in the evaluation image A.

As can further be seen from FIG. 7, other data can also be overlaid in the evaluation image A, for example a first threshold value SW1, a limit time GZP, a factor F and further values. The significance of these values will become evident later.

In accordance with FIGS. 7 and 8, only the sub-area 18 is displayed and output. It is, however, of course also possible to output to the user 6 via the display device 16 the entire evaluation image A, over and above the sub-area 18, and in this case to mark the sub-area 18 appropriately in an analogous manner to that shown in FIG. 3.

In a step S39, the evaluation device 8 then waits for an input from the user 6. When this input has been made, the evaluation device 8 firstly checks in a step S40 whether the input was a confirmation. If this is the case, the evaluation device 8 generates in a step S41 a report with the aid of the evaluation image A and assigns the evaluation image A and the report to the projection images B. It then archives at least the projection images B, the evaluation image A and the report as a unit.

Otherwise, the evaluation device 8 checks in a step S42 whether the input was an instruction to reject the evaluation image A. In this case, the image evaluation method is simply quit without the report being saved.

Otherwise, the evaluation device 8 checks in a step S43 whether the criteria for defining the type and/or the extent of the perfusion are to be changed. If this is the case, in a step S44 the evaluation device 8 receives new criteria and goes back to step S35.

Even if the criteria are not to be changed, the user 6 can have selected only a pixel 9 or a group of pixels 9. In this case, the evaluation device 8 receives in a step S45 a corresponding selection of a pixel 9 or of a group of pixels. In a step S46, it then determines for the selected pixel 9 or for the selected group of pixels the temporal course of the mean value of the corresponding areas of the projection images B by means off which it has determined for the selected pixel 9 or the selected group of pixels the extent of the perfusion, and outputs this course to the user 6 via the display device 16.

Figure 9:
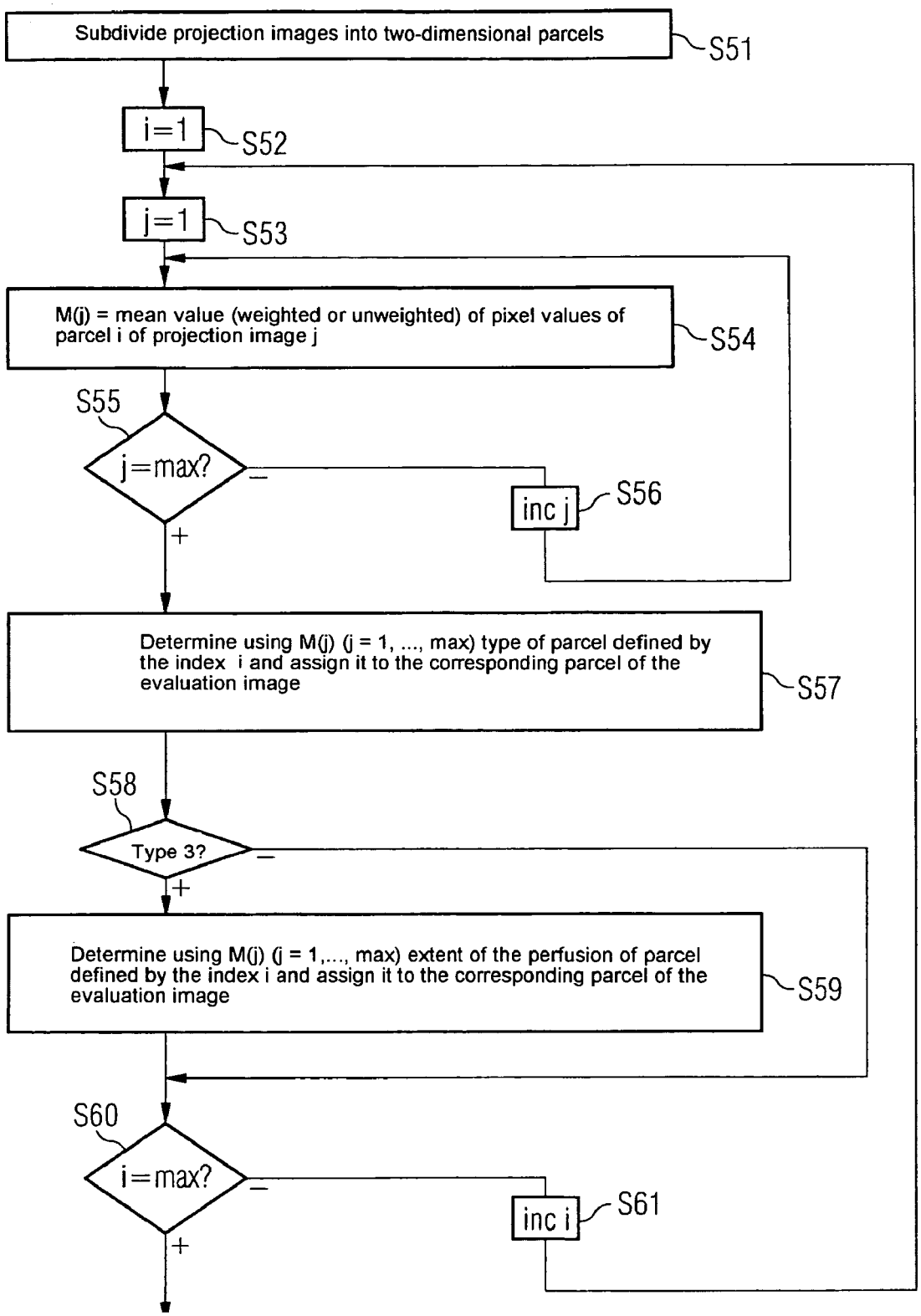
FIG. 9 shows a flow diagram.

FIG. 9 then shows a possible implementation of steps S35 to S37 from FIG. 6.

In accordance with FIG. 9, in a step S51 the evaluation device 8 first subdivides the projection images B into two-dimensional parcels 19. The subdivision of the parcels 19 can be seen, for example, from FIG. 3. According to FIG. 3, the parcels are rectangular. This is the simplest type of subdivision into parcels 19. However, other parcel forms are also possible, in particular equilateral triangles and regular hexagons.

The size of the parcels 19 is in principle freely selectable. However, they must of course be two-dimensional. Furthermore, they should comprise so many pixels 9 that when a mean value is formed the noise tends to be averaged out and motion artifacts are, at least as a general rule, negligible. On the other hand, the resolution should be adequately good. It was determined in trials that the parcels 19 should preferably contain between about 60 and around 1,000 pixels 9, which in the case of rectangular parcels 19 may correspond to an edge length of from e.g. 8×8 pixels 9 to e.g. 32×32 pixels 9.

In steps S52 and S53, the evaluation device 8 next sets the serial indexes i, j to the value one. The index i runs sequentially through each parcel 19 of the two-dimensional arrangement of parcels 19 as shown in FIG. 3. The index j runs sequentially through the projection images B.

In a step S54, the evaluation device 8 determines the—weighted or unweighted—mean value M(j) of the pixel values of the parcel 19 defined by the index i in the projection image B defined by the index j.

In a step S55, the evaluation device 8 checks whether the index j has already reached its maximum value. If this is not the case, the evaluation device 8 increments in a step S56 the index j and goes back to step S54 in order to determine the next mean value M(j).

If all the mean values M(j) are determined for a specific parcel 19, in a step S57 the evaluation device 8 firstly defines with the aid of these mean values M(j) the type of the respective parcel 19 and assigns the determined type to a parcel 19 of the evaluation image A—see FIG. 7. The parcels 19 of the evaluation image A correspond 1:1 to the parcels 19 of the projection images B.

The evaluation device 8 then checks in a step S58 whether the type determined corresponds to type 3, i.e. to the type "perfused part of the surroundings". If this is the case, the evaluation device 8 defines in a step S59 with the aid of the same mean values M(j) the extent of the perfusion for this parcel 19 and assigns it likewise to the corresponding parcel 19 of the evaluation image A.

The evaluation device 8 then checks in a step S60 whether it has already carried out steps S53 to S59 for all the parcels 19. If this is not the case, it increments in a step S61 the index i and goes back to step S53. Otherwise, the determination and assignment of the type and also of the extent of the perfusion is complete.

Figure 10:
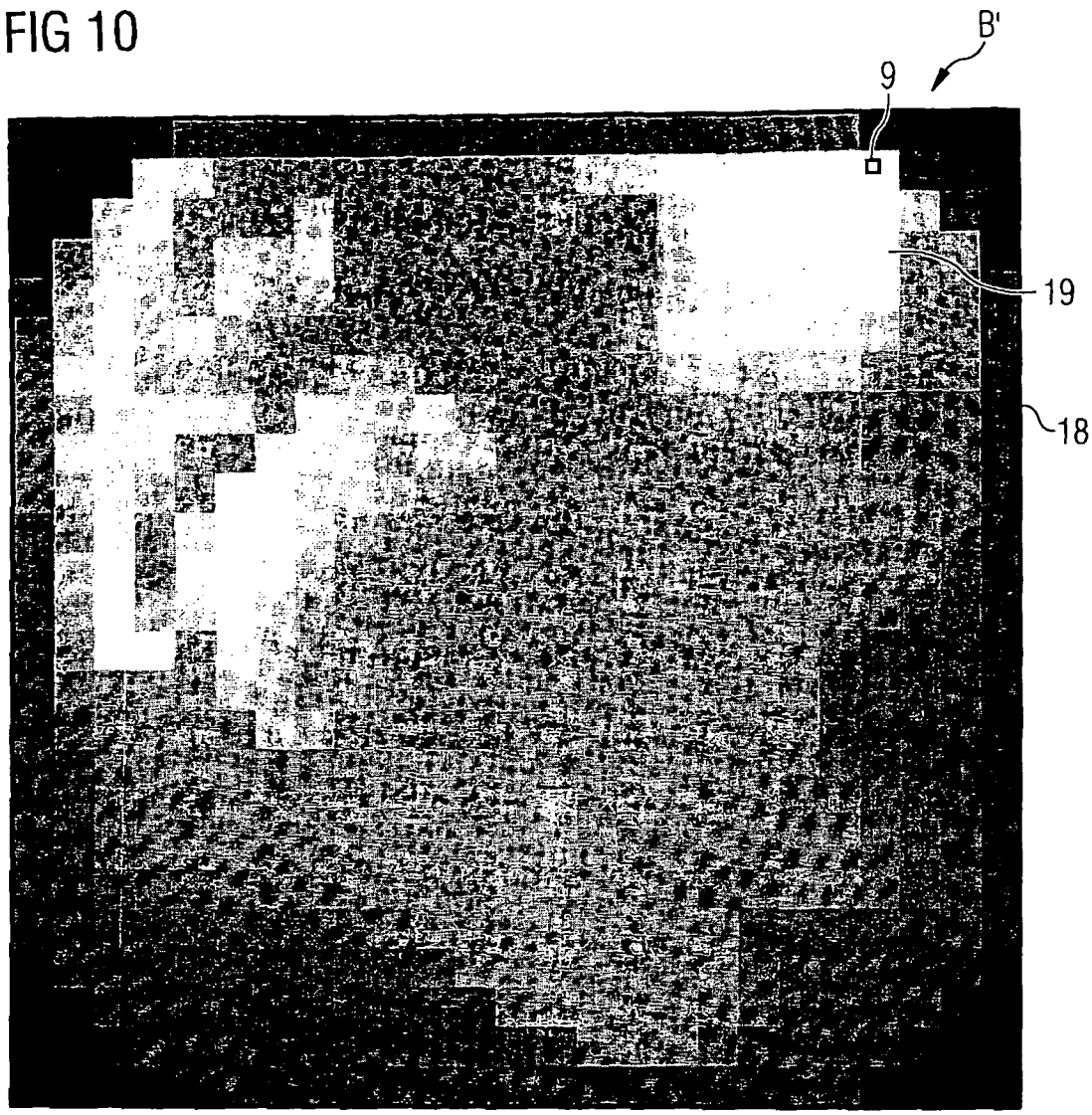
FIG. 10 shows an intermediate image derived from a projection image.

Modifications of the method described above in conjunction with FIG. 9 are of course possible. Thus, for example, in particular the order of the indexes i, j can be swapped. In this case, a number of modified projection images B' are determined. Each of these modified projection images B' has a uniform value per parcel 19, namely the mean value M(j) determined in step S54. An example of a projection image B' modified in this way is shown in FIG. 10.

The procedure according to the invention described above achieves in particular the following features:

The evaluation device 8 performs the assignment of the type with the aid of the temporal course of the pixel values of the projection images B.

The evaluation device 8 performs the assignment of the type and of the extent of the perfusion with the aid of the temporal course of the pixel values of those pixels 9 of the projection images B which lie in a two-dimensional evaluation core 19 of the projection images B defined by the respective pixel 9 of the evaluation image A. For the evaluation core 19 corresponds to the respective parcel 19.

For the same reason, the evaluation device 8 also performs the assignment of type and extent for all the pixels 9 of a parcel 19 uniformly.

Furthermore, the same parcels 19 are used for determining the type and for determining the extent.

FIG. 7 and also FIG. 8 show the outcome of the assignment.

As an alternative to the parcel-by-parcel assignment of type and extent of perfusion of the individual pixels 9 of the evaluation image A, it would of course also be possible for the evaluation device 8 to define for each pixel 9 of the evaluation image A a separate two-dimensional evaluation core in the projection images B, the respective pixel 9 of the evaluation image A being arranged in the center of the respective evaluation core. Even then, a fully analogous procedure is possible. However, a considerable greater computation effort would be required for this and it would not be matched by any significant gain in accuracy.

If a lot of contrast medium is present in the examination object 3, only a relatively limited transmission takes place. This produces a relatively low level of brightness (tending toward black) in the projection images B. Conversely, if only limited contrast medium is present in the examination object 3, a higher level of transmission takes place, as a result of which greater brightness is produced in the projection images B (tending toward white). As a rule, when the projection images B are digitalized, black is assigned the pixel value zero, white the maximum possible pixel value e.g. $2^8-1=255$. The converse of the conventional procedure is followed below. Thus, white is assigned the pixel value zero and black the maximum possible pixel value, as this assignment simplifies understanding of the remarks below. The assignment of zero to white and of the maximum value to black is not, however, required on principle.

Figure 11:
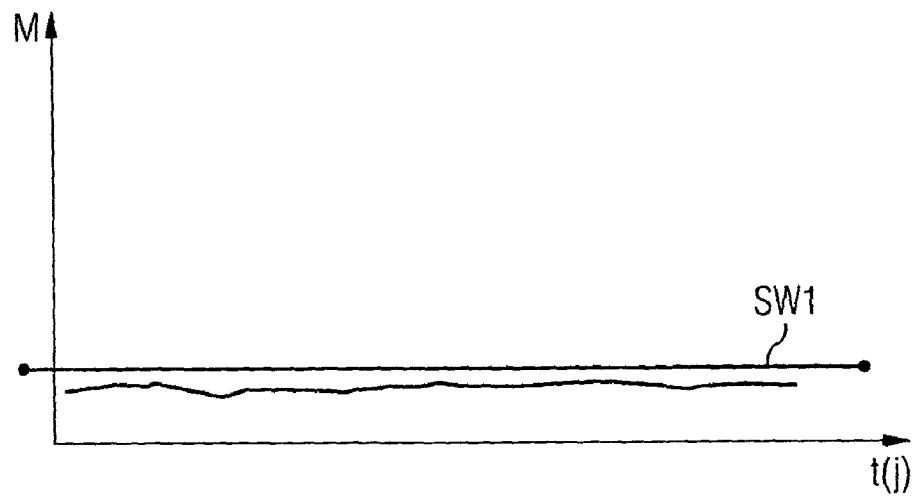
FIGS. 11 to 13 show temporal courses of mean values.

It will now be described in conjunction with FIGS. 11 to 13 how the evaluation device 8 determines the type of the individual parcels 19. For this purpose, the evaluation device 8 needs two decision-making criteria, namely the first threshold value SW1 and the limit time GZP.

If in a specific parcel 19 in all the projection images B the difference of the mean values M(j) determined from the corresponding mean value M(1) of the first projection image B reaches at maximum the threshold value SW1, the type "Background" or "non-perfused part of the surroundings" is assigned to the respective parcel 19. FIG. 11 shows a typical example of such a mean-value course.

The first threshold value SW1 can be firmly prescribed. It can, for example, amount to 5% or 10% of the maximum control range. It can, however, also be defined relative to the mean value M(1) of the respective parcels 19 of the first projection image B. For example, it can amount to 10% or 20% of the mean value M(1). Preferably, however, the first threshold value SW1 depends both on a user 6 input and on the mean value M(1) of the corresponding parcel 19 of the temporally first projection image B. This can be achieved in particular whereby the user 6 specifies in accordance with a step S71 shown in FIG. 14 the factor F for the evaluation device 8 and the evaluation device 8 in a step S72 then defines the first threshold value SW1 for the respective parcel 19 as the product of the factor F and of the mean value M(1) of the respective parcel 19.

If the type of a parcel 19 does not correspond to the type "background", the parcel 19 must either be assigned the type "vessel" or the type "perfused part of the surroundings". The limit time GZP serves to distinguish between these two types: if the first threshold value SW1 is exceeded for the first time before the limit time GZP, the type "vessel" is assigned to a parcel 19, otherwise the type "perfused part of the surroundings" is assigned.

Figure 14:
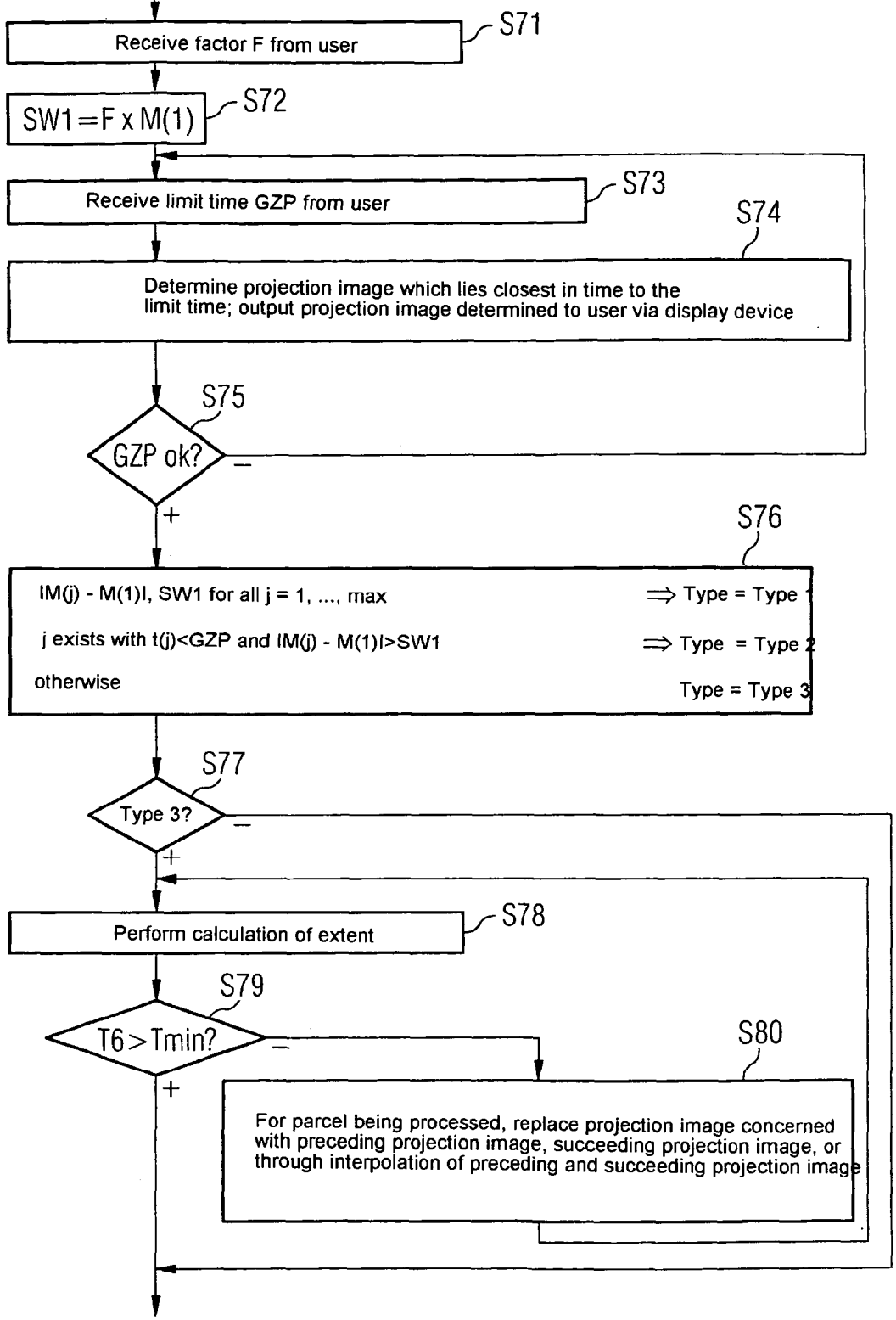
FIG. 14 shows a flow diagram.

The limit time GZP can also be firmly prescribed for the evaluation device 8. Preferably, however, the limit time GZP also depends on a user 6 input. Steps S73 to S75, as shown in FIG. 14, are available for this purpose. In step S73, the evaluation device 8 receives from the user 6 the limit time GZP. In step S74, the evaluation device 8 determines the particular projection image B which lies closest in time to the limit time GZP. It outputs this projection image B as part of step S74 to the user 6 via the display device 16. In step S75, the evaluation device 8 checks whether the user 6 confirms the limit time GZP or whether he/she desires a new specification. Accordingly, either step S73 is returned to or the method proceeds with a step S76 in which the assignment of a type to the individual parcels 19 takes place.

Figure 12:
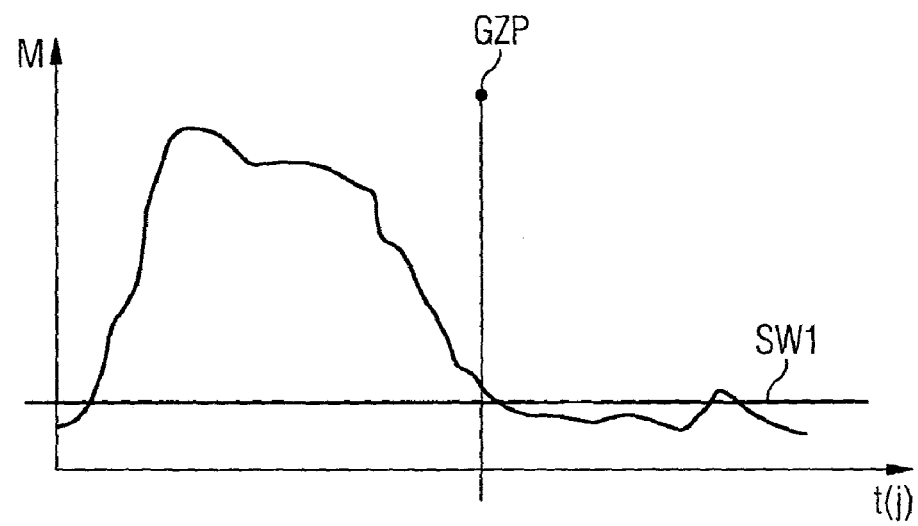
Figure 13:
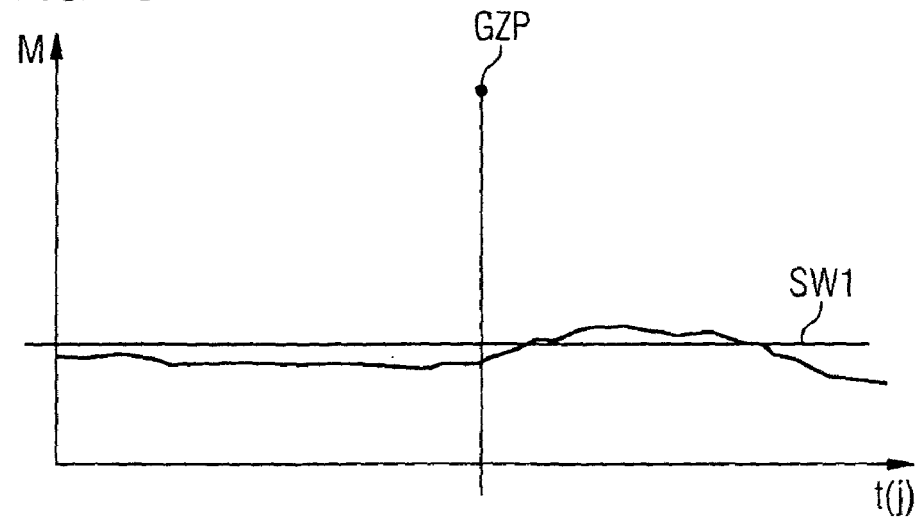

FIGS. 12 and 13 each show an example of a temporal course for a parcel 19 of the type "vessel" and "perfused part of the surroundings" respectively.

In accordance with step S76, the following assignment of types takes place: If for all possible indexes j it is true that the amount of the difference of the mean value M(j) of the projection image B(j) and of the mean value M(1) of the projection image B(1) is less than the first threshold value SW1, type 1 (background) is assigned to the corresponding parcel 19. If a value for the index j exists for which the above-mentioned difference exceeds the first threshold value SW1 and the index j corresponds to a recording time t(j) which lies before the limit time GZP, type 2 (vessel) is assigned to the parcel 19 concerned. Otherwise, type 3 (perfused part of the surroundings) is assigned to the parcel 19 concerned.

In a step S77, the evaluation device 8 checks whether the type determined is type 3. Only if this is the case are steps S78 to S80 carried out. Otherwise, steps S78 to S80 are skipped.

In step S78, the evaluation device 8 performs a calculation of the extent of the perfusion. This calculation can be made in many different ways. This is explained in detail below in conjunction with FIG. 15. However, it should be mentioned in advance that in the simplest case only two or three values are distinguished for the extent of the perfusion, that is only high and low or high, moderate and low. Finer subdivisions are, however, also possible.

Figure 15:
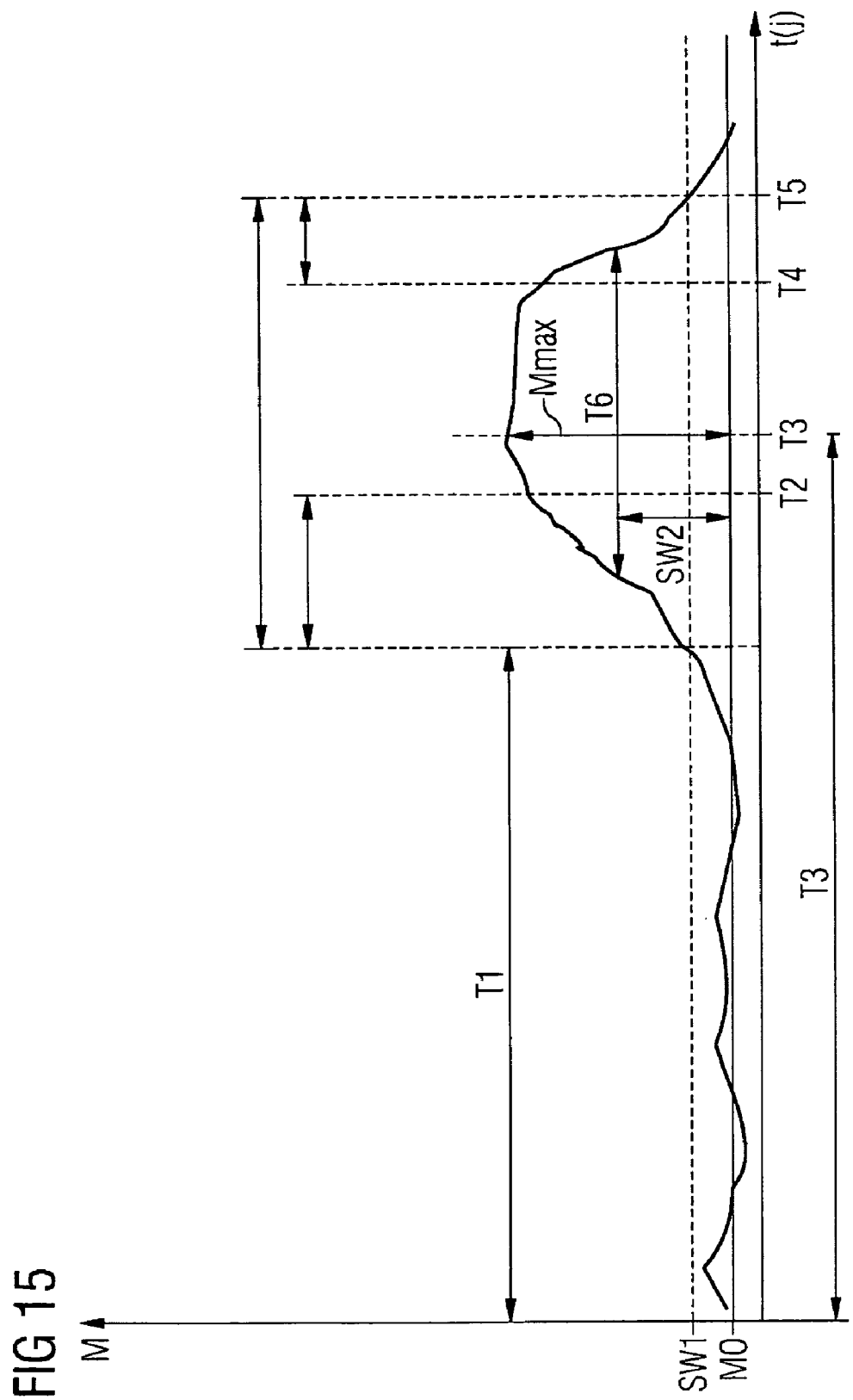
FIG. 15 shows a temporal course of a mean value.

In accordance with FIG. 15, the temporal course of the mean value M in a parcel 19 of type 3 exceeds the first threshold value SW1 for the first time at a time T1. At a time T2, the mean value M reaches e.g. 90% of its maximum Mmax. At a time T3, the mean value M reaches its maximum Mmax. At a time T4, the mean value M falls again to, for example, 90% of its maximum Mmax. At a time T5, the mean value M then falls again below the first threshold value SW1. The numerical value 90% is given only by way of example. A different percentage could of course also be used. Also, a correction by a base value M0 can optionally be carried out. The base value M0 is defined here for the parcel 19 under consideration as the mean value of the mean values M before the limit time GZP or before the time T1.

In addition to the above-mentioned times T1 to T5, an auxiliary time T6 can be defined in which the mean value M exceeds a second threshold value SW2. Here, the second threshold value SW2 corresponds preferably to the so-called FWHM (FWHM=full width at half maximum).

As regards the extent of the perfusion, it is now possible for the evaluation device 8 to determine this from one of these variables or from several of these variables. For example, the following procedures—singly or in combination with one another—are possible:
  The difference of times T5 and T1 is established. This value is characteristic of the time period during which the change in the mean value M exceeds the first threshold value SW1.
  The difference of times T2 and T1 is established. This value is characteristic of the time period of increase in the change in the mean value M.
  The difference of times T5 and T4 is established. This value is characteristic of the time period of decrease in the change in the mean value M.
  The maximum Mmax is used, that is, the maximum change in the mean value M.
  The time T3 is used, that is, the time of the maximum change in the mean value M.
  The time T1 is used, i.e. the period of time until the start of the change in the mean value M.

Of course, modifications and combinations of these procedures are also possible. In the case of combinations, these can alternatively be weighted or unweighted.

Figure 16:

In step S79, the evaluation device 8 checks whether the time period T6 exceeds a minimum time Tmin. If this is not the case, the time period T6 is extremely short. An example of such a course is shown in FIG. 16. This points with high probability to a so-called artifact. The evaluation device 8 therefore skips in this case to step S80. In step S80, it ensures that, with regard to the parcel 19 currently being processed, the corresponding projection image B is ignored. In the simplest case, the respective projection image B (restricted, of course, to the respective parcel 19) is simply omitted. Preferably, however, the evaluation device 8 performs a replacement. It replaces the parcel 19 being processed with the corresponding parcel 19 of the projection image B immediately preceding in time, of the projection image B immediately succeeding in time or with an interpolation of the projection images B immediately preceding in time and immediately succeeding in time.

As a general rule, the minimum time Tmin will correspond to a single projection image B, possibly also two projection images B. If the minimum time Tmin corresponds to a single projection image B, the obvious solution is to replace an artifact-encumbered parcel 19 with the mean value of the corresponding parcels 19 of the projection images B immediately preceding in time and immediately succeeding in time. If the minimum time Tmin corresponds to two projection images B, a further distinction has to be made to establish whether the time period T6 corresponds to one or two projection images B. If the time period T6 corresponds to one projection image B, the above-mentioned interpolation can be performed. If the time period T6 corresponds to two projection images B, either an interpolation with the weighting 2:1 or 1:2 can be carried out or a replacement made with the corresponding parcel 19 of the respective projection image B immediately adjacent in time.

After step S80 has been executed, the evaluation device 8 goes back to step S78.

The inventive image evaluation method described hereinabove can optionally be refined as required. For example, it is possible, after the extent of the perfusion has been determined parcel by parcel, to perform a finer determination. This is described in detail below in conjunction with FIG. 17.

Figure 17:
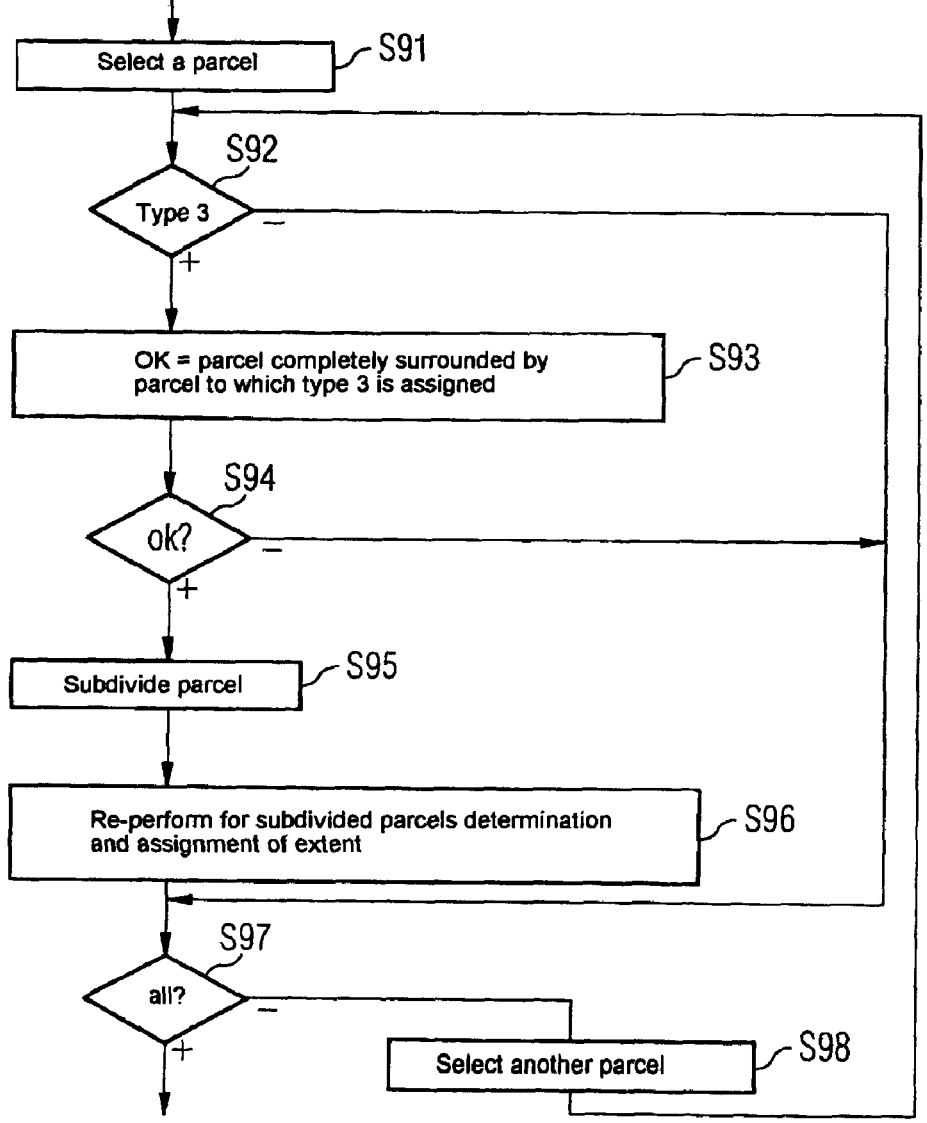

As shown in FIG. 17, the evaluation device 8 first selects in a step S91 a parcel 19. In a step S92, the evaluation device 8 checks whether type 3 is assigned to the selected parcel 19. Only if this is the case is the move to a step S93 made. In step S93, the evaluation device 8 calculates the auxiliary logical variable OK. The auxiliary logical variable OK assumes the value "true" if, and only if, the selected parcel 19 is completely surrounded by parcels 19 to which type 3 is also assigned. The value of the auxiliary logical variable OK is checked in step S94. Depending on the result of the check, steps S95 and S96 are then executed. In step S95, the selected parcel 19 is subdivided, for example into 2×2=4 sub-parcels. For each sub-parcel the evaluation device 8 then carries out afresh in step S96 a determination and assignment of the extent of the perfusion.

In step S97, the evaluation device 8 checks whether it has already carried out steps S92 to S96 for all the parcels 19. If this is not the case, it moves on to a step S98 by selecting a different, previously not yet selected, parcel 19. From step S98, it goes back to step S92.

The procedure shown in FIG. 17 can, of course, be modified. Thus, for example, step S95 can be brought forward before step S91 so that it is carried out for all the parcels 19. Steps S91 to S94 and S97 and S98 are then performed with the sub-parcels respectively. Irrespective of whether the one or the other procedure is adopted, however, the evaluation device 8 determines afresh the extent of perfusion only for those pixels 9 of the evaluation image A to which the type "perfused part of the surroundings" is assigned and which are surrounded within a predetermined minimum distance (here a parcel 19 or a sub-parcel) exclusively by pixels 9 to which the type "perfused part of the surroundings" is also assigned.

In the context of the above explanation of the image evaluation method according to the invention it was assumed that the recording parameters of the recording arrangement 1, including the operating parameters of the radiation source 4, would be held constant during the recording of the images B. If, on the other hand, this prerequisite is not fulfilled, brightness fluctuations can occur in the recorded images B which can impair the evaluation, and in extreme cases even render it impossible. Within the scope of the present invention, there is therefore provision for carrying out appropriate corrections so that an evaluation can nevertheless take place. These corrections occur here before step S35 or after step S44 in FIG. 6. They are explained in detail below in conjunction with FIG. 18.

As shown in FIG. 18, in a step S101 a reference area 20 of the projection images B is firstly defined. In the simplest case, the definition of the reference area 20 is effected by means of an appropriate user input. The evaluation device 8 then overlays in a step S102 the reference area 20 into one of the projection images B. This can be seen for example in FIG. 3.

Next, in a step S103 the evaluation device 8 defines one of the projection images B as the reference image B. Which of the projection images B is defined as the reference image B, is in principle random. As a rule, however, the first or the last of the projection images B is defined as the reference image B.

In a step S104, the evaluation device 8 then selects one of the projection images B.

The evaluation device 8 compares in a step S105 the selected projection image B with the reference image B. The comparison is carried out only within the reference areas 20 that correspond to one another. With the aid of the comparison, the evaluation device 8 specifies in a step S106 a transformation of the pixel values of the selected projection image B. The transformation is specified such that the mean value of the pixels 9 of the reference area 20 of the transformed projection image B on the one hand and the mean value of the pixels 9 of the reference image B on the other have a predetermined functional relationship to one another. The functional relationship can consist, in particular, in the fact that the mean value of the pixels 9 of the reference area 20 of the transformed projection image B is equal to the mean value of the pixels 9 of the reference image B. The transformation can alternatively be linear or non-linear.

In accordance with the transformation specified in step S106, the evaluation device 8 transforms in a step S107 all the pixels 9 of the selected projection image B, i.e. both the pixels 9 inside the reference area 20 and the pixels 9 outside the reference area 20.

In a step S108, the evaluation device 8 checks whether it has already carried out steps S104 to S107 for all the projection images B. If this is not yet the case, it moves on first to a step S109 in which it selects another of the projection images B. It then goes back to step S105. Otherwise, the transformation of the projection images B is complete.

As an alternative to specification of the reference area 20 by the user 6, it is of course also possible for the evaluation device 8 to determine the reference area 20 automatically. For example, the evaluation device 8 can determine the reference area 20 from the pixels 9 of the evaluation image A to which it has assigned the type "non-perfused part of the surroundings", that is, type 1. Parcels 19 which lie outside the exposure area are not included. This can, as shown in FIG. 19 for example, occur as follows:

Firstly, in a step S111 the evaluation device 8 selects a parcel 19. In a step S112, the evaluation device 8 then checks whether the selected parcel 19 is of type 1. Only if this is the case are steps S113 to S115 executed. Otherwise, There is a skip direct to step S116.

In step S113, the evaluation device 8 determines the auxiliary logical variable OK. The auxiliary logical variable OK assumes the value "true" only if the selected parcel 19 is completely surrounded by parcels 19 to which type 1 is also assigned. This procedure achieves in particular the outcome that only the central area of the evaluation image A can be specified as the reference area 20. The peripheral area on the other hand is compulsorily masked out.

The value of the auxiliary logical variable OK is checked in step S114. If the auxiliary logical variable OK has the value "false", there is a jump direct to step S116, otherwise step S115 is executed. In step S115, the evaluation device 8 defines the selected parcel 19 as an integral part of the reference area 20.

In a step S117, the evaluation device 8 checks whether it has already checked off all the parcels 19. If this is not yet the case, it goes on to step S118 in which it selects another parcel 19. It then goes back to step S112. Otherwise, the method for defining the reference area 20 is complete. The reference area 20 defined in this way is then transferred onto the projection images B.

If the evaluation device 8 defines the reference area 20 automatically, it is also possible, as an alternative to or in addition to the procedure shown in FIG. 19, to proceed in the manner described below in conjunction with FIG. 20.

In accordance with FIG. 20, the evaluation device 8 calls up in a step S121 information about the recording geometry and/or about the location of entry of the contrast medium. Based upon this data, the evaluation device 8 can then in a step S122 select specific parcels 19 as belonging to the reference area 20.

Furthermore, it is of course possible to output the reference area 20 in accordance with FIG. 3 to the user 6 via the display device 16. The user 6 is consequently able to check, confirm, reject or optionally also modify the reference area 20.

The image evaluation method according to the invention represents a considerable advance in relation to image evaluation methods of the prior art. In particular, it is not necessary in the case of the image evaluation method according to the invention to work with DSA images. While this is possible, it is not actually necessary. It is also not necessary to define an ROI (region of interest). It is also not necessary to define which parts of the projection images B are a vessel, a perfused part of the surroundings or a non-perfused part of the surroundings. Rather, this definition is performed by the evaluation device 8 itself. It is also not necessary to define or to have available a reference image. Furthermore, no image warping of any kind has to be carried out.

The image evaluation method according to the invention exhibits a high degree of automation and a high processing speed. In addition, it is very flexible, including in the context of visualization of the evaluation results and in the context of interactivity. Finally, it is also possible to integrate the image evaluation method to form part of a TIMI flow measurement. The duplicate recording of projection images B, together with the associated X-ray stress on the patient 3, can in this way be avoided.

The invention claimed is:

1. An image evaluation method for a two-dimensional projection image of an examination object containing a vascular system and a surroundings thereof, comprising:
    displaying a temporal course of a distribution of a contrast medium in the examination object by the projection image having a plurality of pixels with pixel values defined by an area of the examination object;
    determining a two-dimensional evaluation image based on the projection image having a plurality of pixels corresponding to the pixels of the projection image via a computer and outputting the evaluation image to a user via a display device;
    determining a type for each of the pixels in a sub-area of the evaluation image and assigning the determined type to the pixel, the type:
        characteristic of whether the pixel corresponding to a vessel of the vascular system, a perfused part of the surroundings or a non-perfused part of the surroundings,
        determined from the temporal course of the pixel values of the pixels of the projection image which is in a two-dimensional type evaluation core defined by a respective pixel of the evaluation image; and
    determining an extent of a perfusion of a corresponding area of the examination object in the pixels of the evaluation image assigned the type of perfused part of the surroundings and assigning the extent to the respective pixel, the extent determined from the temporal course of the pixel values of the pixels of the projection image which is in a two-dimensional basic extent-evaluation core defined by a respective pixel of the evaluation image,
    wherein the computer:
    determines the extent in the pixels of the evaluation image assigned the type of perfused part of the surroundings and in the pixels surrounded within a predetermined minimum distance of the pixels assigned the type of perfused part of the surroundings, and
    assigns the extent from the temporal course of the pixel values of the pixels of the projection image which is in an additional extent-evaluation core contained in a corresponding basic extent-evaluation core of the projection image defined by a respective pixel of the evaluation image.

2. The image evaluation method as claimed in claim 1, wherein the projection image is selected from a series of images of an iteratively moving examination object and a phase information about the examination object is assigned to each image in the series which deviates by a maximum of one phase boundary from a reference phase with the phase boundary or the reference phase input from the user,
    wherein the selected projection image together with the phase information or with the deviation of the phase information assigned to the projection image is output to the user via the computer to the display device.

3. The image evaluation method as claimed in claim 1, wherein the sub-area is input by the user and marked in the projection image or in the evaluation image.

4. The image evaluation method as claimed in claim 1, wherein the computer:
    subdivides the sub-area of the evaluation image into type parcels each having several pixels and assigns the type parcel by parcel,
    determines a mean value of the type evaluation core corresponding to a respective type parcel for the projection image and assigns the type based on the temporal course of the mean value,
    determines a maximum change of the mean value of the type evaluation core relative to a mean value of a temporally first type evaluation core,
    if the maximum change of the mean value is less than a first threshold value input from the user:
        assigns the type of non-perfused part of the surroundings to a respective pixel of the evaluation image, or
    if the maximum change of the mean value exceeds the first threshold value:
        determines a temporally earliest projection image in which a difference of the mean value of the type evaluation core between the projection image and a temporally first projection image exceeds the first threshold value, and assigns the type of vessel or the type of perfused part of the surroundings to a respective pixel of the evaluation image depending on whether a time of the temporally earliest projection image is before or after a limit time input from the user.

5. The image evaluation method as claimed in claim 4, wherein the projection image is selected in a closest time to the limit time and output to the user via the display device to visually check the limit time.

6. The image evaluation method as claimed in claim 1, wherein the computer:

subdivides the sub-area of the evaluation image into extent parcels each having several pixels and assigns the extent on a parcel-by-parcel basis, determines a mean value of the basic extent-evaluation core corresponding to a respective extent parcel and assigns the extent based on the temporal course of the mean value.

7. The image evaluation method as claimed in claim 6, wherein the extent of the perfusion is determined by a variable selected from the group consisting of: time period during which a change in the mean value exceeds the first threshold value, time period during which a change of the mean value increases, time period during which a change of the mean value decreases, maximum change of the mean value, time period of the maximum change of the mean value, and time period until a start of a change of the mean value.

8. The image evaluation method as claimed in claim 7, wherein the computer:

determines a time period during which the change in the mean value exceeds a second threshold value, compares the time period with a minimum time period, ignores a respective basic extent-evaluation core if the time period is below the minimum time period, determines a replacement evaluation core from a basic extent-evaluation core which is immediately before or after a time of the ignored basic extent-evaluation core, and replaces the ignored basic extent-evaluation core with the replacement evaluation core, and assigns the extent anew.

9. The image evaluation method as claimed in claim 1, wherein the basic extent-evaluation core is identical to the type evaluation core.

10. The image evaluation method as claimed in claim 1, wherein the computer converts the extent of the perfusion of the evaluation image into color values based on an assignment rule and outputs the evaluation image in a color-coded representation together with the assignment rule to the user via the display device.

11. The image evaluation method as claimed in claim 1, wherein the computer:

defines a reference image from a series of images from which the projection image is selected, compares a reference area of the projection image with a corresponding reference area of the reference image, defines a valid transformation of the pixel values of the projection image based on the comparison, transforms the pixel values according to the transformation so that a mean value of the pixel values of the reference area of the transformed projection image and of the reference image having a predetermined functional relationship, and overlays the reference area in the projection image or in the evaluation image.

12. The image evaluation method as claimed in claim 11, wherein the reference area is defined automatically by the computer from the pixels of the evaluation image assigned the type of non-perfused part of the surroundings and includes information about a recording geometry on which the projection image is based and a location of entry of the contrast medium into the examination object.

13. The image evaluation method as claimed in claim 11, wherein the reference area is defined by the user.

14. The image evaluation method as claimed in claim 1, wherein the computer:

receives from the user a selection of a pixel or of a group of pixels of the evaluation image, determines the temporal course of the pixel values of areas of the projection images based on the extent of the perfusion of the selected pixel or of the selected group of pixels, and outputs the temporal course to the user via the display device.

15. The image evaluation method as claimed in claim 1, wherein the computer outputs defining criteria which defines the type of the sub-area of the evaluation image together with the evaluation image to the user via the display device and re-determines the evaluation image if the defining criteria is modified interactively by the user.

16. The image evaluation method as claimed in claim 1, wherein the computer overlays the projection image into the evaluation image.

17. The image evaluation method as claimed in claim 1, wherein the computer automatically generates a report, assigns the evaluation image and the report to the projection image, and archives the projection image, the evaluation image and the report as a unit based on a request of the user.

18. A computer program embodied on a computer readable data medium for performing an image evaluation for a two-dimensional projection image of an examination object containing a vascular system and a surroundings thereof, comprising:

a computer sub program that displays a course of a distribution of a contrast medium in the examination object by the projection image having a plurality of pixels with pixel values defined by an area of the examination object;

a computer sub program that determines a two-dimensional evaluation image based on the projection image having a plurality of pixels corresponding to the pixels of the projection image via a computer and outputs the evaluation image to a user via a display device;

a computer sub program that determines a type for each of the pixels in a sub-area of the evaluation image and assigns the determined type to the pixel, the type characteristic of whether the pixel corresponding to a vessel of the vascular system, a perfused part of the surroundings or a non-perfused part of the surroundings;

a computer sub program that determines an extent of a perfusion of a corresponding area of the examination object in the pixels of the evaluation image assigned the type of perfused part of the surroundings and assigns the extent to the respective pixels;

a computer sub program that determines the extent in the pixels of the evaluation image assigned the type of perfused part of the surroundings and in the pixels surrounded within a predetermined minimum distance of the pixels assigned the type of perfused part of the surroundings; and a computer sub program that assigns the extent from the temporal course of the pixel values of the pixels of the projection image which is in an additional extent-evaluation core contained in a corresponding basic extent-evaluation core of the projection image defined by a respective pixel of the evaluation image, wherein the type and the extent are determined from the course of the pixel values of the pixels of the projection image which is in a two-dimensional evaluation core defined by a respective pixel of the evaluation image.

19. A computer for performing an image evaluation for a two-dimensional projection image of an examination object containing a vascular system and a surroundings thereof, comprising:

an interface unit which introduces a data medium storing a computer program which performs the image evaluation to the computer, the computer program comprising:

a computer sub program that displays a course of a distribution of a contrast medium in the examination object by the projection image having a plurality of pixels with pixel values defined by an area of the examination object, a computer sub program that determines a two-dimensional evaluation image based on the projection image having a plurality of pixels corresponding to the pixels of the projection image via a computer and outputs the evaluation image to a user via a display device, a computer sub program that determines a type for each of the pixels in a sub-area of the evaluation image and assigns the determined type to the pixel, the type characteristic of whether the pixel corresponding to a vessel of the vascular system, a perfused part of the surroundings or a non-perfused part of the surroundings, a computer sub program that determines an extent of a perfusion of a corresponding area of the examination object in the pixels of the evaluation image assigned the type of perfused part of the surroundings and assigns the extent to the respective pixel, a computer sub program that determines the extent in the pixels of the evaluation image assigned the type of perfused part of the surroundings and in the pixels surrounded within a predetermined minimum distance of the pixels assigned the type of perfused part of the surroundings, and a computer sub program that assigns the extent from the temporal course of the pixel values of the pixels of the projection image which is in an additional extent-evaluation core contained in a corresponding basic extent-evaluation core of the projection image defined by a respective pixel of the evaluation image, wherein the type and the extent are determined from the course of the pixel values of the pixels of the projection image which is in a two-dimensional evaluation core defined by a respective pixel of the evaluation image;

a memory unit which reads and executes the computer program; and a display device which displays the projection image and the evaluation image.

* * * * *